(12) United States Patent
Tripier et al.

(10) Patent No.: US 9,315,511 B2
(45) Date of Patent: Apr. 19, 2016

(54) METHODS FOR PREPARING FUNCTIONAL TETRAAZACYCLOALKANE COMPOUNDS USING A SPECIFIC CYCLIC BISAMINAL COMPOUND

(71) Applicants: UNIVERSITE DE BRETAGNE OCCIDENTALE, Brest (FR); CENTRE NATIONAL DE LA RECHERCHE SCIENTIFIQUE (CNRS), Paris (FR)

(72) Inventors: Raphael Tripier, Kersaint Plabennec (FR); Nathalie Camus, Brest (FR)

(73) Assignees: UNIVERSITE DE BRETAGNE OCCIDENTALE, Brest (FR); CNRS—CENTRE NATIONAL DE LA RECHERCHE, Paris (FR)

( * ) Notice: Subject to any disclaimer, the term of this patent is extended or adjusted under 35 U.S.C. 154(b) by 0 days.

(21) Appl. No.: 14/358,423

(22) PCT Filed: Nov. 16, 2012

(86) PCT No.: PCT/EP2012/072898
§ 371 (c)(1),
(2) Date: May 15, 2014

(87) PCT Pub. No.: WO2013/072491
PCT Pub. Date: May 23, 2013

(65) Prior Publication Data
US 2014/0323717 A1 Oct. 30, 2014

(30) Foreign Application Priority Data
Nov. 16, 2011 (FR) ...................................... 11 60426

(51) Int. Cl.
*C07D 487/22* (2006.01)
*C07D 257/02* (2006.01)
*C07D 487/08* (2006.01)

(52) U.S. Cl.
CPC ............ *C07D 487/22* (2013.01); *C07D 257/02* (2013.01); *C07D 487/08* (2013.01)

(58) Field of Classification Search
CPC ... C07D 487/22; C07D 257/02; C07D 487/04
USPC ......................................... 540/460; 544/247
See application file for complete search history.

(56) References Cited

U.S. PATENT DOCUMENTS 7,312,327 B2    12/2007   Boschetti
2006/0217548 A1  9/2006   Boschetti

OTHER PUBLICATIONS

Written Opinion of the International Searching Authority; Application No. PCT/EP2012/056390; 8 pages; Oct. 8, 2013; WIPO, Geneva Switzerland.
Marine Antoine et al: "Synthesis and NMR Characterisation of New Cyclam-glyoxal Diamides"; Journal of the Chemical Society, Perkin Transactions 2, No. 3, pp. 552-555; published online Jan. 23, 2002; DOI: 10.1039/B109307J.
Takenouchi K. et al: "Novel Bifunctional Macrocyclic Chelating Agents Appended with a Pendant-type Carboxymethylamino Ligand and Nitrobenzyl Group and Stability of the 88Y (III) Complexes"; Journal of Organic Chemistry, Americal Chemical Society, Easton U.S.; vol. 58, No. 7; Jan. 1, 1993; pp. 1955-1958; DOI: 10.1021/jo00059a062.

*Primary Examiner* — Paul V Ward
(74) *Attorney, Agent, or Firm* — Thomas Horstemeyer, LLP

(57) ABSTRACT

Special C-functionalized cyclic bisaminal compounds having formula (I) or (II), their salts or solvates, methods for their preparation, their uses, and methods for preparing functional tetraazacycloalkane compounds implementing such cyclic bisaminal compounds.

14 Claims, No Drawings

METHODS FOR PREPARING FUNCTIONAL TETRAAZACYCLOALKANE COMPOUNDS USING A SPECIFIC CYCLIC BISAMINAL COMPOUND

CROSS-REFERENCE TO RELATED APPLICATION

This application is the 35 U.S.C. §371 national stage of PCT Application No. PCT/EP2012/072898, filed Nov. 16, 2012, which is herein incorporated by reference in its entirety and which also claims priority to, and the benefit of French patent application 1160426, filed Nov. 16, 2011, which is incorporated herein by reference in its entirety.

The field of the invention is that of the synthesis of functional tetraazacycloalkane compounds, especially cyclam derivatives. These compounds can be polyfunctional and especially bifunctional.

More specifically, the invention pertains to a particular cyclic bisaminal compound from which methods are derived for preparing cyclam derivatives according to the invention, as well as methods for preparing this compound.

The chemistry of cyclic polyamines and especially tetraazacycloalkanes, the two main representatives of which are 1,4,7,10-tetraazacyclododecane (cyclen) and 1,4,8,11-tetraazacyclotetradecane (cyclam) have expanded considerably in these last decades.

Through the free doublets of these secondary amines, these nitrogen macrocycles can form highly stable complexes with numerous cations and especially the transition metals. The chelating capacity of these compounds can be improved or again it can be extended to other metals such as the lanthanides or the heavy metals using functional groups, and especially particular ligands having affinity with these cations or metals. By functionalizing these macrocycles, i.e. by grafting one or more functional groups, especially coordinating groups (ligands) onto them, it is possible to modify the complexing properties of the macrocycle, its affinity and its selectivity relative to a given element, its solubility. It is thus possible for example to obtain molecules capable of being grafted to a solid support or to a nanoparticle or of being vectored towards target cells or organs, for example by grafting on to a biological vector such as an antibody, a haptene or a peptide. It is also possible to give these macrocycles a luminescent property such as fluorescence.

Depending on the properties sought, the cyclam or cyclen derivatives obtained can be used in numerous applications, in a wide variety of fields such as catalysis, magnetism, materials, purification of liquids and gases, methods of analysis and detection, medicine, especially nuclear medicine.

Cyclam and cyclen derivatives, known as cross-bridge and side-bridge derivatives, which correspond to tetraazacyclododecane having a bridged structure (an ethylene bridge), respectively between two opposite and adjacent nitrogen atoms of the macrocycle, are especially an interesting target in the therapeutical field, especially in the development of radiopharmaceuticals. Owing to their special structure, they are capable of forming a highly stable metallic complex without "jettisoning" metal into the organism.

Nitrogen macrocycles can be functionalized in three different ways: either directly on one of the nitrogen atoms (N-functionalization) of the macrocycle, or on a ligand bound to one of the nitrogen atoms of the macrocycle or on a carbon atom (C-functionalization) of the macrocycle. However, the first method of synthesis has the drawback of causing the loss or reduction of the chelating properties of the macrocycle in making one or more free doublets of the nitrogen atom of the macrocycle unavailable, and does not enable access to functionalized "cross-bridge" and "side-bridge" derivatives. The second method of synthesis has the drawback of modifying or hindering the function of the ligand obtained from a first functionalizing of the macrocycle. Our research has therefore been directed towards the last method of synthesis which has the advantage, as compared with the other modes of synthesis, of enabling the grafting of a functional group, enabling for example the coupling of the macrocycle to a support (coupling function) without modifying the chelating properties of the macrocycle or altering the structure and the properties of other ligands linked to the macrocycle. This method of synthesis is particularly valuable for obtaining polyfunctional macrocycles, especially bifunctional macrocycles, capable of chelating a metal atom or cation on the one hand and of being grafted onto a given element (support, nanoparticle, biomolecule) on the other hand, i.e. possessing at least one coordinating function and at least one coupling function. This last method of synthesis, which appears to be simple in theory, is seen to have several difficulties in its practical implementation.

The most usual and oldest methods rely on a direct cyclization of the macrocycles from pre-functionalized synthons. The drawback of these methods is that the size of the macrocycle and the nature of the coupling function cannot be applied on an extensive scale. This is a drawback for industrial-scale implementation. Certain of these methods are described for example in the patent application WO 03/029228.

In particular, there is a known way described in this patent WO 03/029228 for preparing cyclam derivatives from a tetraamine and a dicarbonyl compound. The bisaminal intermediate obtained is then cyclized by means of a dihalogen reagent in the presence of $K_2CO_3$ in acetonitrile. While this method gives a satisfactory cyclization yield (greater than or equal to 50%), it has the drawback of using large quantities of acetonitrile, making this method costly, unfriendly to the environment and unsuited for transposition to the industrial level.

The present Applicant has now discovered new methods for preparing functional tetraazacycloalkane compounds, especially cyclam derivatives and more particularly methods for preparing functional tetraazacycloalkane compounds that do not have the drawbacks of the prior art, and are particularly environment friendly and economically interesting (in terms of cost of solvents and energy), simple to implement and suited to industrial-scale implementation.

Most of the steps of the methods according to the invention, especially those used to cyclize the tetranitrogen compound, can be done in protic solvents, such as preferably water and/or methanol in small quantities, at relatively low temperatures (below or equal to 100° C., preferably below 60° C., and or, even better, below 50° C.).

These methods according to the invention are thus more environment friendly and require little energy to be implemented.

The methods according to the invention furthermore comprise a limited number of steps.

They necessitate no difficult step of purification.

They result in satisfactory yields, especially of cyclization (at least 50%).

Advantageously, the cyclization of these compounds can be obtained as a "one-pot" reaction, i.e. in situ in a same reaction medium. In particular, they can be done without separation and/or without intermediate purification.

A first object of the invention therefore relates to a C-functionalized cyclic bisaminal compound and the method of preparation. Obtaining this compound is a key step in the synthesis of functional tetraazacycloalkane compounds, and especially cyclam derivatives, especially bifunctional cyclam derivatives capable of chelating an atom or metal cation and of being grafted onto a given substrate. It enables both the cyclization of the macrocycle and the grafting of a functional group on its carbon skeleton.

A second object of the invention relates to methods for preparing particular C-functionalized and/or N-functionalized cyclic compounds, the methods implementing a C-functionalized cyclic bisaminal compound according to the invention.

Other objects, aspects, features or advantages of the invention shall appear more clearly from the following description and from the examples.

The term "cyclic" is understood to mean that the compound comprises at least one cyclic group in its structure, where said cycle can be saturated or unsaturated, aromatic or non-aromatic, comprising preferably five to six members such as for example a phenyl or pyrrol group. Unless otherwise stated in the present application, the term "cyclic" shall be used to designate equally well a monocyclic or a polycyclic group.

The C-functionalized bisaminal cyclic compound according to the invention meets the formula (I) or (II), its solvates or one of its salts:

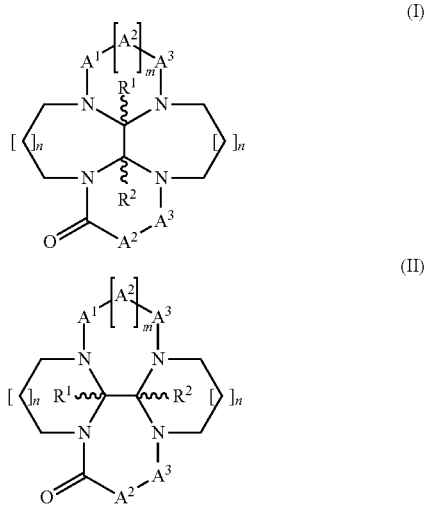

wherein:
  $R^1$ and $R^2$, identical or different, represent a hydrogen atom, a C1-C4 alkyl group, preferably methyl, or, together with the carbon atoms of the bisaminal bridge to which they are linked, they can form a saturated or unsaturated, six-membered hydrocarbon cyclic group such as for example a phenyl or cyclohexane group, preferably a cyclohexane group,
  m and n, identical or different, are equal to 0 or to 1;
  $A^1, A^2, A^3, A'^2, A'^3$, identical or different, are chosen from the groups $CH_2$, CHR and C=O; on condition that $A'^2$ or $A'^3$ designates a CHR group;
  the group or groups R, identical or different, can designate any functional group, or functional group precursor, whatsoever.

The term "functional group" is understood to mean a group conferring special properties on the cyclic compound, as described for example in the introduction to the present application, namely a group capable of modifying the complexing properties of the cyclic compound, its affinity and its selectivity relative to a given element, its solubility, capable of grafting or coupling the cyclic compound to a support (solid, nanoparticle, biological vector) and capable of conferring properties of luminescence. In particular, the functional group can be a coupling function, namely a reactive function enabling the creation of a stable carbon-carbon or heteroatom-carbon stable bond. The functional group can possess or not possess one or more coordinating functions that give the carrier molecule of the functional group complexing properties that may be improved relative to a given substrate. The functional group possessing one or more coordinate functions is also called a ligand.

The term "functional group precursor" is understood to mean a group that needs to be transformed by one or more chemical reactions, for example an alkylation or a treatment in acid medium, to obtain a functional group.

In the formula (I) or (II), m is preferably equal to 1.

Preferably, $R^1$ and $R^2$ are chosen from amongst a hydrogen atom or a metal group or else, together with the carbon atoms of the bisaminal bridge with which they are linked, they form a cyclohexane group. More preferably, they are chosen from amongst a hydrogen atom and a methyl group.

According to a first embodiment, $A'^3$ designates a CHR group.

According to a second embodiment, $A'^2$ designates a CHR group.

Preferably, the invention uses a compound having the following formula (III), one of its salts or solvates:

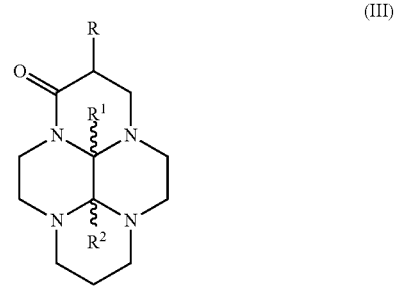

wherein:
  R, $R^1$, $R^2$ are as defined in the formulae (I) and (II).

The group or groups R of the formulae (I), (II) or (III) can be ionic or non-ionic.

In particular, they can be chosen independently of each other from amongst the following:
  a hydrocarbon group, saturated or unsaturated, straight or branched, cyclic or acyclic, comprising 1 to 30 carbon atoms, preferably linear and 8 to 20 carbon atoms, and comprising, as the case may be, one or more heteroatoms, such as O, N, S, P or a halogen,
  a group V, V being chosen from amongst a halogen, a nitrile, $NR^5R^6$, $NO_2$, $OR^7$, COX, NHCOX, $—CONR^5R^6$, $(O)_sPO(OR^8)(OR^9)$, s being an integer ranging from 0 to 1, X being a halogen or a group $OR^5$; $R^5, R^6, R^7, R^8$ and $R^9$ being chosen from amongst a hydrogen atom and a straight or branched, saturated or unsaturated $C_1$-$C_{30}$ alkyl group,
  a group W, W being a cyclic hydrocarbon group that can be monocyclic, bicyclic or tricyclic, saturated or unsaturated, the cycle or cycles comprising 5 to 6 members, and at least one of them being capable of being substituted by one or more groups chosen from amongst N-chlorosuccinimide, P(C$_6$H$_5$)$_2$, P(O)(C$_6$H$_5$)$_2$, (CH$_2$)$_p$ V, p being an integer ranging from 0 to 4 and/or being capable of forming, with one or more carbon atoms of the cycle, one or more ketone functions, a group Y, Y being a heterocyclic group, capable of being monocyclic, bicyclic or tricyclic, saturated or unsaturated, the cycle or cycles comprising five to six members, and at least one of them being capable of being substituted on at least one or more carbon atoms or heteroatoms by one or more groups chosen from amongst the groups V and W, a straight or branched, saturated or unsaturated, preferably C$_1$-C$_{30}$, alkyl group substituted by one or more groups V and/or W, a trityl group; the heterocycle group being capable of forming, with one or more carbon atoms of the cycle, one or more ketone functions, a straight or branched, saturated or unsaturated C$_1$-C$_{30}$ alkyl group substituted by one or more groups, V, W, and/or Y.

Preferably, the group or groups R are chosen according to the properties of functions that are to be conferred on the compound (I), (II) or (III). R being chosen so as to increase the affinity, the selectivity of the cyclen or the cyclam with a given element such as a cation, an anionic complex or a metal atom, an organic or inorganic solid support, a nanoparticle, a biomolecule (antibody, haptene, peptide, sugar, etc).

By way of an example, R can be chosen from among:

hydrophobic groups such as for example saturated or unsaturated, straight or branched, cyclic or acylic hydrocarbon groups comprising at least one linear hydrocarbon chain having 8 to 30 carbon atoms, hydrophilic groups such as those comprising at least one glycol ethylene group, for example glycol ethylene or glycol polyethylene, tensioactive groups, such as for example lipid/phospholipid type groups, fluorescent groups, such as for example anthracene, phenanthrene, phenanthroline, mesitylBODIPY, ionic groups, such as guadinidium or arsenium type organic groups, groups bearing at least one primary, secondary or tertiary amine function, possibly protected by the usual protection systems (Boc, tosyl (Ts), etc), groups bearing at least one alcohol function, groups bearing at least one alkene and/or alkyne function, groups bearing at least one amide function, groups bearing at least cyano, nitrile, CF$_3$ function, groups bearing at least one acid, ester, aldehyde function.

Among all the compounds having formula (I), (II) or (III) that are usable, the compounds preferred are those for which the group or groups R are chosen from amongst the groups (CH$_2$)$_i$X with i being an integer equal to 0 or 1, X being a group chosen from amongst a halogen atom, a hydroxyl, CH$_2$OH, COOH, COOCH$_3$, COOC$_2$H$_5$. In particular, it is preferred to use compounds having formula (III) wherein: R$^1$ and R$^2$, which are identical or different, represent a hydrogen atom, a C$_1$-C$_4$ alkyl group or can form, together with the carbon atoms of the bisaminal bridge to which they are linked, a saturated or unsaturated hydrocarbon cyclic group with six carbon atoms; R is a (CH$_2$)$_i$X group with i being an integer equal to 0 or 1, X being a group chosen from amongst a halogen atom, a hydroxyl, CH$_2$OH, COOH, COOCH$_3$, COOC$_2$H$_5$.

The invention also covers the stereoisomers of the above-described C-functionalized bisaminal cyclic functions, especially the enantiomers and diastereoisomers.

The groups R$^1$ and R$^2$ are preferably positioned so as to limit the steric hindrance that can appear between the different substituents of cyclam and its derivatives. They can be positioned in the cis or trans position, in the endo or exo position, relative to the carbon skeleton of the cyclam or cyclen. Preferably, the groups R$^1$ and R$^2$ are in the cis position.

According to one particular embodiment, the compound having formula (I) or (II) according to the invention can comprise at least two amide functions, preferably at least one of the groups A$_1$, A$_2$ or A$_3$ designates a group C=O. Preferably, A$_1$ or A$_3$ designates a group C=O. When A$_1$ or A$_3$ designates a group C=O, the di-oxo functions of the compound having formula (I) or (II) according to the invention are in the cis or trans position.

The following formulae serve to illustrate compounds according to the invention having such configurations.

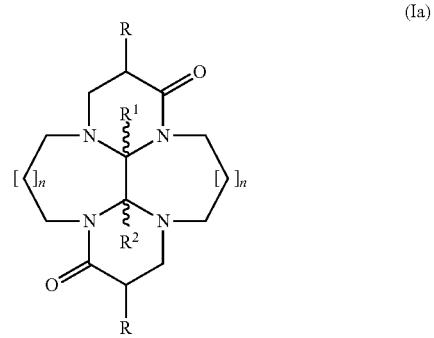

(Ia)

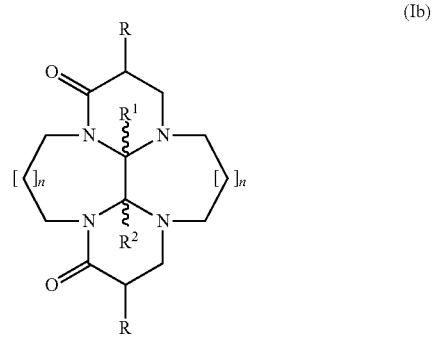

(Ib)

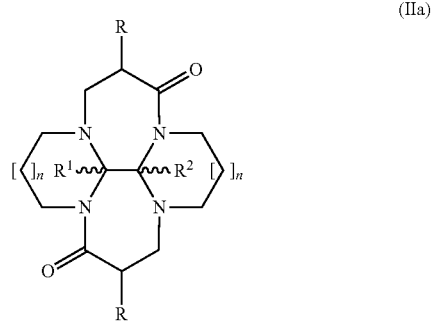

(IIa)

(IIb)
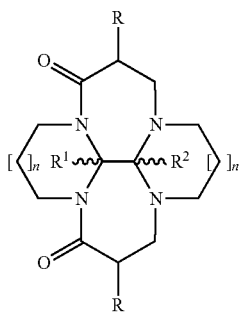

(Ic)
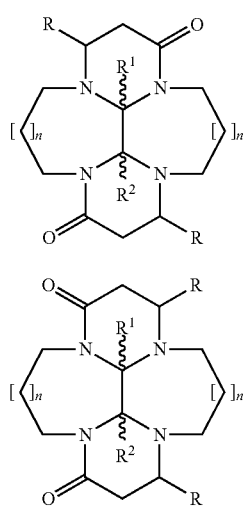

(Id)

(IIc)

(IId)

(Ie)
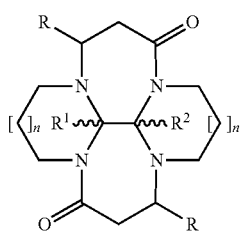

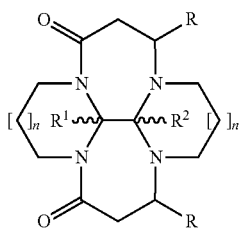

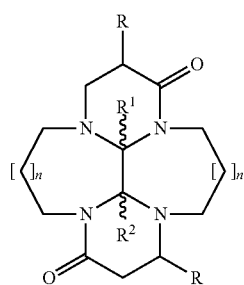

(If)
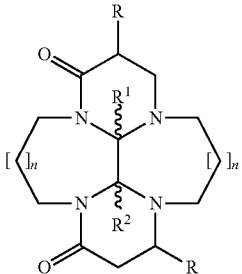

(IIe)
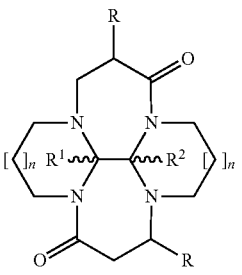

(IIf)
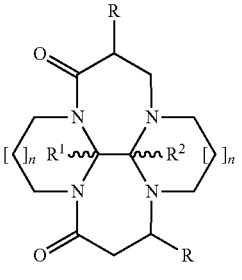

these are formulae according to which: R, $R^1$ and $R^2$, n are as defined in the formulae (I) or (II).

An object of the invention is also a method for preparing a C-functionalized cyclic bisaminal compound as defined here above comprising:

(i) a step during which a tetramine having formula (VII) is made to react (VII)
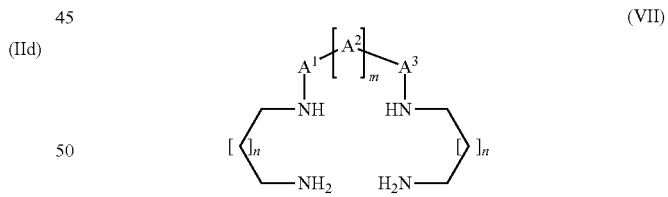

wherein: $A^1$, $A^2$, $A^3$ are chosen among from the groups $CH_2$, CHR and C=O, and preferably the groups $CH_2$, m and n, identical or different, are equal to 0 or 1, with a dicarbonyl compound having formula (IV):

(IV)
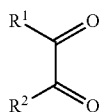

wherein: $R^1$ and $R^2$, identical or different, represent a hydrogen atom, a $C_1$-$C_4$ alkyl group, preferably methyl, or can together form, with the carbon atoms to which they are linked, a saturated or unsaturated cyclic hydrocarbon group with six carbon atoms, such as a phenyl or cyclohexane group, and preferably a cyclohexane group,
to form a bisaminal intermediate having formula (VIII) or (IX) or a mixture of these compounds:

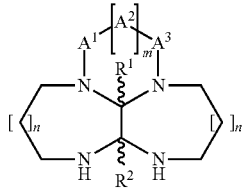

(VIII)

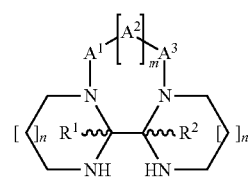

(IX)

formulae (VIII) and (IX) wherein: $A^1$, $A^2$, $A^3$, m, n are as defined in the formula (VII) and $R^1$ and $R^2$ are as defined in the formula (IV);
  (ii) then a step during which the intermediate or intermediates obtained are made to react with a cyclizing agent meeting the formula (VI), preferably in a protic solvent:

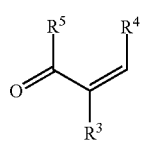

(VI)

formula (VI) wherein:
  $R^3$ and $R^4$, which are identical or different, can be chosen from amongst a hydrogen atom and the group R as defined in the formula (I) or (II); and
  $R^5$ represents a hydroxyl, a halogen, an alcoxyl such as mesyl, tosyl; or
  $R^5$ can form with $R^3$ or $R^4$ a heterocyclic group having five to six members.
Preferably, this step (i) and/or (ii) take place in a protic medium (or solvent).
  An object of the invention is also a method for preparing a cyclic bisaminal compound as defined here above, comprising:
  (i) a step during which at least two equivalents of ethylene diamine or propylene diamine are made to react with at least one equivalent of a dicarbonyl compound having formula (IV) as defined here above,
to form a bisaminal intermediate having formula (V) or (V') or a mixture of these compounds:

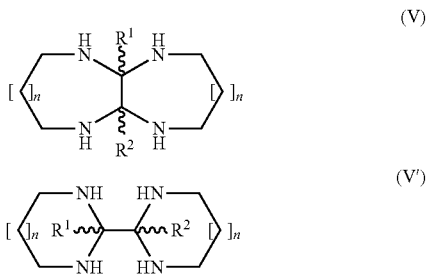

formulae (V) and (V') wherein $R^1$ and $R^2$ are as defined in the formula (IV);
  (ii) then a step during which the intermediate obtained is made to interact with a first cyclizing agent,
  (iii) and a step during which the novel intermediate obtained is made to react with the second cyclizing agent, where the steps (ii) and (iii) can be performed simultaneously or successively, the cyclizing agent can be identical or different and at least one of the two cyclizing agents meets the formula (VI) as defined here above.

As a cyclizing agent different from the usable cyclizing agents having formula (VI), we can cite any classic cyclizing agent capable of cyclizing the compounds (V) and (V'), for example a compound Q-$CH_2CH_2CH_2$-Q' with Q and Q' being chosen from amongst the leaving group such as halogens or a tosylate group. Preferably, the step or the steps (i), (ii) and/or (iii) take place in a protic medium (or solvent). More specifically, the step or the steps bringing into play a cyclizing agent having formula (VI) take place in the protic medium.

According to one particular embodiment, when the intermediate that has formula (V) and/or (V') is made to react with cyclizing agents having formula (VI) that are identical or different, a compound having formula (I') and/or (II') is obtained.

The compound having formula (I') corresponds to a compound having formula (I) wherein:
  $A^1$ or $A^3$ designate a group C=O and:
    if $A^1$ designates C=O and m is equal to 0, then $A^3$ designates CHR, or if $A^3$ designates C=O and m is equal to 0, then $A^1$ designates CHR;
    or if $A^3$ designates C=O and m is equal to 1, then $A^2$ or $A^3$ designates CHR, or if $A^1$ designates C=O and m is equal to 1, then $A^2$ or $A^3$ designates CHR;
R complying with any one of the definitions mentioned here above.
  The compounds having formula (I') are illustrated for example by the compounds having formula (Ia) to (If) described further above.
  The compounds having formula (II') correspond to a compound having formula (II) wherein:
  $A^1$ or $A^3$ designates a group C=O and:
    if $A^1$ designates C=O and m is equal to 0, then $A^3$ designates CHR, or if $A^3$ designates C=O and m is equal to 0, then $A^1$ designates CHR;
    or if $A^3$ designates C=O and m is equal to 1, then $A^2$ or $A^3$ designates CHR, or if $A^1$ designates C=O and m is equal to 1, then $A^2$ or $A^3$ designates CHR;

R meeting any one of the definitions indicated here above.

The compounds having formula (II') are illustrated for example by the compounds having formula (IIa) to (IIf) described further above.

According to another particular embodiment, when the intermediate having formula (V) is made to react with the cyclizing agent having formula (VI) and a different cyclizing agent, a compound is obtained having the formula (I") and/or (II") as defined here below:

The compound having formula (I") corresponds to a compound having formula (I) wherein:
when $A^1$ designates C=O and m is equal to 0, then $A^3$ designates $CH_2$ or C=O; or when $A^3$ designates C=O and m is equal to 0, then $A^1$ designates $CH_2$ or C=O;
when $A^3$ designates C=O and m is equal to 1, then $A^2$ and $A^3$ are chosen from amongst the groups $CH_2$ and C=O; or when $A^1$ designates C=O and m is equal to 1, then $A^2$ and $A^3$ are chosen from among the groups $CH_2$ and C=O.

The compound having formula (II") corresponds to a compound having formula (II) wherein:
when $A^1$ designates C=O and m is equal to 0, then $A^3$ designates $CH_2$ or C=O; or when $A^3$ designates C=O and m is equal to 0, then $A^1$ designates $CH_2$ or C=O;
when $A^3$ designates C=O and is equal to 1, then $A^2$ and $A^3$ are chosen from amongst the groups $CH_2$ and C=O; or when $A^1$ designates C=O and m is equal to 1, then $A^2$ and $A^3$ are chosen amongst the groups $CH_2$ and C=O.

When, in the formula (VI), $R^5$ forms a heterocyclic group with $R^3$ or $R^4$, this heterocyclic group responds preferably to one having the following formulae (X) or (XI):

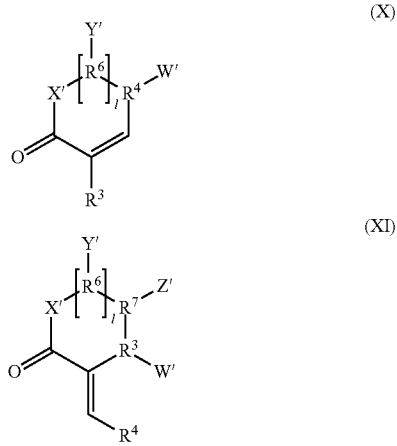

formula (X) wherein: $R^3$ is a group R as defined in the formulae (I) or (II),
X' is an oxygen atom,
Y' and W', identical or different, are chosen from amongst a hydrogen atom, a straight or branched, saturated or unsaturated $C_1$-$C_{30}$ alkyl group.
l is equal to 0 or 1, with
when l is equal to 0, the group X' is linked to the group $R^4$ and $R^4$ forming with W' a group $CH_2$ or C=O,
when l is equal 1, $R^4$ and $R^6$ together form, with the groups Y' and W', the groups $CH_2$—$CH_2$, CH=CH, $CH_2$(C=O), (C=O)$CH_2$ or a phenyl group;
formula (XI) in which: $R^4$ is a group R as defined in the formula (I) or (II),
X' is an oxygen atom,
W', Y' and Z', identical or different, are chosen from amongst a hydrogen atom, a straight or branched, saturated or unsaturated $C_1$-$C_{30}$ alkyl group.
$R^3$, $R^6$ and $R^7$ designate $CH_2$ groups,
l is equal to 0 or 1, and
when l is equal to 1,
$R^3$ and $R^7$ can together form, with the groups Z' and W', the groups: $CH_2$—$CH_2$, CH=CH, or a phenyl group, and/or
$R^6$ and $R^7$ can together form, with the groups Y' and Z', the groups: $CH_2$—$CH_2$, CH=CH, or a phenyl group;
when l is equal to 0, the group X' is linked to the group $R^7$.

In the methods described here above, the steps (i), (ii) and/or (iii) preferably take place in a same medium, more preferably in a protic solvent. Examples of protic solvents that can be used are water, lower ($C_1$-$C_4$) alcohols, such as methanol, ethanol, propanol and butanol.

The methods of preparation thus obtained are environment-friendly. They can be done in "one pot", i.e. in situ in a same reaction medium. In particular, the steps (i), (ii) and/or (iii) can be done without intermediate separation or purification.

The steps (i), (ii) and/or (iii) can be implemented at temperatures T1 and T2, below or equal to 100° C. with T1 being lower than T2. Preferably, the temperature T1 is below 30° C., and more preferably it varies from 0 to 25° C. The temperature T2 is chosen preferably as being the reflux temperature of the solvent in the reaction medium. Preferably, it is below 60° C., and better still it is below 50° C.

Advantageously, the step or the steps implementing the cyclizing agent or agents, especially the step implementing the cyclizing agent having formula (VI), can be performed by applying microwaves. This makes it possible to increase the reaction speed and therefore to shorten the reaction time. The reaction can for example be assisted by microwaves.

The invention also relates to various C-functionalized and/or N-functionalized tetranitrogen cyclic compounds derived from cyclam, that can be obtained from a compound having formula (I), (II), one of its salts, solvates or their mixture, as defined here above, as well as their methods of preparation.

The method or methods for preparing C-functionalized and/or N-functionalized tetranitrogen cyclic compounds, derived from cyclam, from a compound having formula (I), (II), one of its salts, solvates or their mixture according to the invention comprise at least one of the following steps:
A) substituting one or more nitrogen atoms of the compound having formula (I) and/or (II) by one or more groups R", identical or different, preferably identical, where R" can designate any functional group or functional group precursor as defined here above or any amine function protector group, for example by means of an electrophilic agent R"Q, Q being a leaving group, such as a halogen atom, a tosylate group, and/or by means of at least one Michael reagent that is a carrier of the group R".
B) reducing one or more ketone functions in alpha position of one of the four nitrogen atoms of the compound having formula (I) and/or (II), for example by one or more reducing agents that are identical or different, said compounds having formula (I) and/or (II) being possibly modified by one or more steps A) and/or C).
C) deprotecting the bisaminal bridge of the compound (I) and/or (II), for example by means of one or more reducing agents that are identical or different, said compounds having formula (I) and/or (II) being possibly modified by one or more steps A) and/or B).

The step for deprotecting C) can be total or partial, depending on the nature of the reducing agent used.

Examples of a reducing agent that can be used for the partial deprotecting of the bisaminal bridge include selective reducing agents such as sodium borohydride (NaBH$_4$), hydrazine hydrate or sodium hydroxide. In particular, NaBH$_4$ will preferably be used to obtain a cis-reduction of the amines of the bisaminal bridge. In particular, hydrazine hydrate or sodium hydroxide will preferably be used to obtain a trans-reduction of the amines of the bisaminal bridge. The preparation schemes described further below will illustrate the regioselectivity of the partial deprotection steps depending on the nature of the reducing agent used.

Examples of reducing agents that can be used for the partial deprotection of the bisaminal bridge include strong reducing agents such as lithium hydride (LiAlH$_4$), or BH$_3$ in tetrahydrofuran (THF).

The steps B) and C) can be performed simultaneously or separately by using for example a same reducing agent or different reducing agents.

When at least one of the groups R" cited in the step A) designates an amine function protecting group, for example a benzyl group, then the step A) can be followed by a step D) for deprotection of the amine function by means of an appropriate deprotecting agent. For example, when R" is a benzyl group, the step D) of deprotection can be done by means of a hydrogenolysis, for example catalyzed by palladium on coal.

When at least one of the groups R" cited in the step A) designates a precursor group of a functional group, then the step A) can be followed by a subsequent step enabling the conversion of R" into a functional group, for example a treatment in acid medium enabling an ester to be converted into carboxylic acid.

According to a first variant, the invention relates to a method for preparing a C-functionalized compound having the following formula (XII), one of its salts, solvates or their mixture:

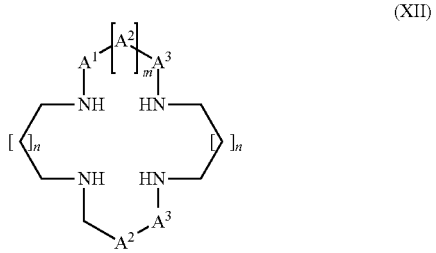

(XII)

wherein: $A^1, A^2, A^3, A'^2, A'^3$, m and n, are as defined in the formula (I) or (II), said method comprising a step for reducing the compound having formula (I) or (II), or their mixture.

The reduction step is carried out by means of a reducing agent.

Examples of reducing agents that can be used in this method of preparation are lithium hydride (LiAlH$_4$), the borohydrides such as BH$_3$ in tetrahydrofuran.

According to second variant, the invention relates to a method for preparing C and N-tetra-functionalized compounds having the following formula (XIII), one of its salts, solvates or their mixture:

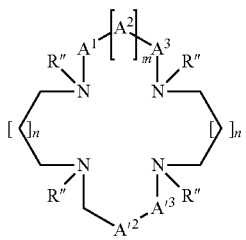

(XIII)

wherein: $A^1, A^2, A^3, A'^2, A'^3$, m and n are as defined in the formula (I), or (II), where the groups R", which are identical or different, preferably identical, can designate any functional group whatsoever that is a precursor of a functional group or protecting group, said method comprising the following steps:

i) reducing a compound having formula (I) or (II) as defined here above or their mixture, by means of at least one reducing agent, and finally ii) substituting, simultaneously or successively, on the four nitrogen atoms of the tetranitrogen cycle of the compound having a reduced formula (I) or (II) or reduced formulae (I) and (II) in the event of mixture, by groups R", that are identical or different, for example by means of at least one electrophilic agent R"Q, Q being a leaving group, such as a halogen atom, a tosylate group and/or by means of at least one carrier Michael reagent of the group R".

In particular, the group or groups R" having formula (XIII) can designate a functional group or a precursor of a functional group as defined here above, preferably possessing at least one coordination function and/or a protecting group of a nitrogen atom of the tetranitrogen cyclic compound.

The group or groups R" can be chosen from amongst the functional groups possessing at least one coordination function, for example a chelator of ions, especially metal ions such as acid, amine, alcohol, imine, phosphonate, amide, 2,6-pyridine and its isomers, tetrazol, sulphur derivatives such as thiazol, propanoate, acetate, propanol, indazol.

The R" group or groups can also be functional group precursors such as a tertiobutyl ester, for example a tertiobutyl acid. The tertiobutyl ester must be processed in an acid medium (HCl) to obtain the corresponding acid functional group.

The R" group or groups can also be amine function protective groups of the cyclic tetranitrogen compound such as benzyl groups. These groups serve especially to induce or favor the regioselectivity of a subsequent reaction, and are inert enough not to react during this reaction step. These groups can then be cleaved by an appropriate deprotection reaction. When the group R" is a benzyl group, it can be deprotected by hydrogenolysis, especially by catalytic hydrogenolysis on palladium on coal.

Examples of reducing agents that can be used in this preparation method are lithium hydride (LiAlH$_4$), borohydrides such as BH$_3$ in tetrahydrofuran.

In a third variant, the invention relates to a method for preparing a C-functionalized and N-mono-functionalized compound having the following formula (XIV), one of its salts, solvates or their mixture:

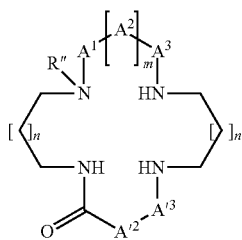

(XIV)

wherein: $A^1, A^2, A^3, A'^2, A'^3$, m and n are as defined in the formula (I) or (II), the group R" is as defined in the formula (XIII), said group comprising:
(i) substituting a nitrogen atom of a compound having formula (I) or (II) or their mixture by a protective group R", for example by means of an electrophilic agent R"Q, Q being a leaving group as defined here above, and then
(ii) deprotecting the bisaminal bridge with hydrazine hydrate or sodium hydroxide.

The substitution at the step (i) leads especially to the formation of the following cationic intermediates (XIV-1) and/or (XIV-2):

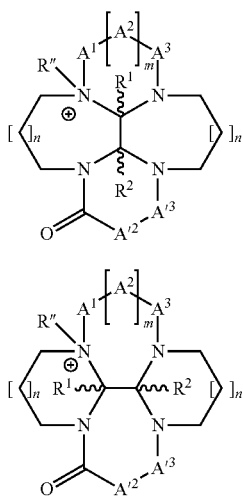

(XIV-1)

(XIV-2)

wherein: $A^1, A^2, A^3, A'^2, A'^3, R^1$ and $R^2$, m and n are as defined in the formula (I) or (II) and R" as defined in the formula (XIII).

The compound (XIV) can be reduced subsequently by means of an appropriate reducing agent such as $BH_3$ in THF to prepare a C-functionalized and N-monofunctionalized compound having formula (XIV), one of its salts, solvates or their mixture:

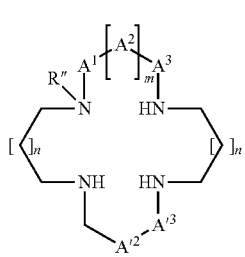

(XIV')

wherein: $A^1, A^2, A^3, A'^2, A'^3$, R", m and n are as defined in the formula (XIV-1) or (XIV-2).

According to a fourth variant, the invention relates to a method for preparing a C-functionalized and N-di-trans-functionalized compound having the following formula (XV), one of its salts, solvates or their mixture:

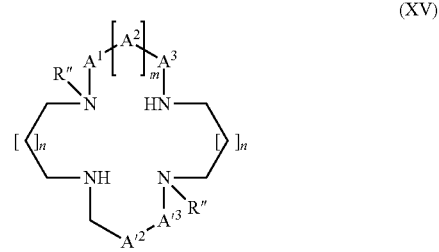

(XV)

wherein: $A^1, A^2, A^3, A'^2, A'^3$, m and n are as defined in the formula (I) or (II), the groups R", which are identical or different, preferably identical, are as defined in the formula (XIII), said method comprising the following steps:
(i) reducing a compound having formula (I) or (II) as defined here above or their mixture by means of a selective reducing agent, then
(ii) substituting on two non-adjacent nitrogen atoms of the tetranitrogen cycle of the compound having a reduced formula (I) or (II) or reduced formulae (I) and (II), reduced in case of mixture, by groups R", for example by means of at least one electrophilic agent R"Q, Q being a leaving group as defined here above, and finally
(iii) deprotecting the bisaminal bridge with hydrazine hydrate or sodium hydroxide.

Examples of selective reducing agents that can be used are sodium borohydride ($NaBH_4$). The selective reducing agent reduces the ketone function of the tetranitrogen cycle (I) or (II) without deprotecting the bisamine function.

The term "non-adjacent nitrogen atoms of the cycle" is understood to mean that these constituent nitrogen atoms of the tetraazacycloalkane cycle are separated by a constituent nitrogen atom of the cycle.

The substitution at the step (ii) leads especially to the formation of the following cation intermediates (XV-1) and/or (XV-2):

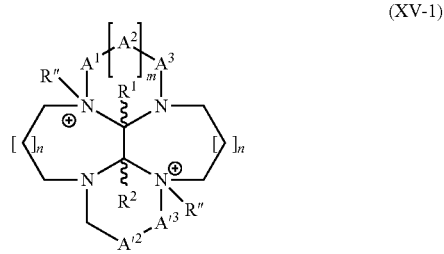

(XV-1)

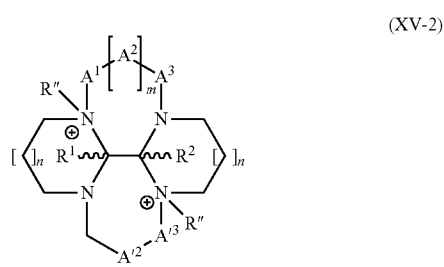

(XV-2)

wherein: $A^1, A^2, A^3, A'^2, A'^3, R^1$ and $R^2$, m and n are as defined in the formula (I) or (II).

When, in the formula (XV), R" designates a protector group such as a benzyl group, the compound having formula (XV) can be used as a starting reagent to prepare a C-functionalized and N-di-trans-functionalized compound having the following formula (XV'), one of its salts, solvates or their mixture:

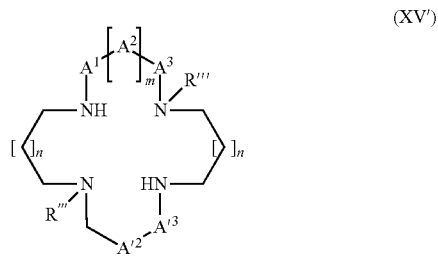

(XV')

wherein: $A^1, A^2, A^3, A'^2, A'^3$, m and n are as defined in the formula (I) or (II), the groups R''', which are identical or different, preferably identical, correspond to functional groups or precursors of functional groups R" as defined in the formula (XIII).

The compound (XV') can be prepared by implementing the steps (i) to (iii) as described here above for example, and then in implementing the following steps:

(iv) substituting the two non-substituted secondary amines of the tetranitrogen cycle having formula (XV) by groups R''' as defined here above, for example by means of an electrophilic agent R'''Q, Q being a leaving group as defined here above, then (v) deprotecting the protecting groups R".

When R" is a benzyl group, the step (v) of deprotection can be done by means of hydrogenolysis for example, catalyzed by palladium on coal.

According to a fifth variant, the invention relates to a method for preparing a compound known as a C-functionalized and N-di-trans-functionalized "cross bridge" compound having the following formula (XVI), one of its salts, solvates or their mixture:

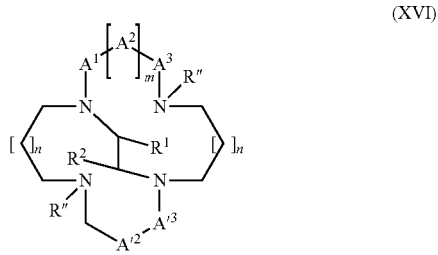

(XVI)

wherein: $A^1, A^2, A^3, A'^2, A'^3, R^1$ and $R^2$, m and n are as defined in the formula (I) or (II), the groups R", which are identical or different, preferably identical, are as defined in the formula (XIII) said method comprising the following steps:

(i) reducing a compound having formula (I) or (II) as defined here above, or their mixture, by means of a selective reducing agent, and then (ii) substituting the secondary amines of the reduced cycle (I) or (II), or of the reduced cycles (I) and (II), in the case of mixture, by groups R" as defined here above, for example by means of an electrophilic agent R"Q, Q being a leaving group as defined here above, and finally (iii) partially reducing the bisaminal bridge by means of a selective reducing agent.

An example of a selective reducing agents that can be used in the steps (i) and (iii), is sodium borohydride ($NaBH_4$).

At the step (i), the selective reducing agent reduces the ketone function of the tetranitrogen cycle (I) or (II) without deprotecting the bisamine function.

At the step (iii), the selective reducing agent partially reduces the bisaminal bridge.

The substitution at the step (ii) leads especially to the formation of the following cationic intermediates (XVI-1) and/or (XVI-2):

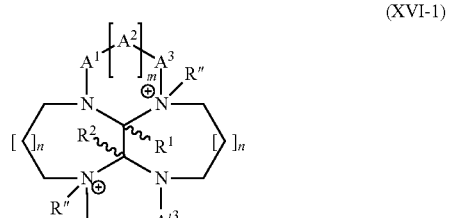

(XVI-1)

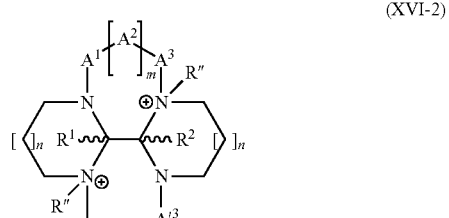

(XVI-2)

wherein: $A^1, A^2, A^3, A'^2, A'^3, R^1$ and $R^2$, m and n are as defined in the formula (I) or (II), R" as defined in the formula (XIII).

When, in the formula (XVI), R" is a protective group such as benzyl, it can be deprotected after the step (iii) by means of hydrogenolysis, for example catalyzed by palladium on coal.

According to a sixth variant, the invention relates to a method for preparing a compound known as a N-mono-functionalized side-bridge compound having the following formula (XVII), one of its salts, solvates or their mixture:

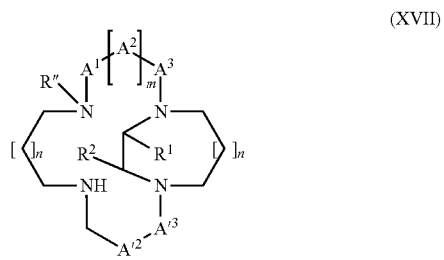

(XVII)

formula (XVII) wherein: $A^1, A^2, A^3, A'^2, A'^3, R^1$ and $R^2$, m and n are as defined in the formula (I) or (II), the group R" is as defined in the formula (XIII), said method comprising the following steps:
(i) substituting a secondary amine of the compound having formula (I) and/or (II) by a group R" as defined in the formula (XIII), for example by means of an electrophilic agent R"Q, Q being a leaving group as defined here above, then
(ii) partially reducing the bisaminal bridge by means of a selective reducing agent such as NaBH$_4$.

The substitution at the step (i) leads especially to the formation of the cationic intermediates (XVII-1) and/or (XVII-2) as follows:

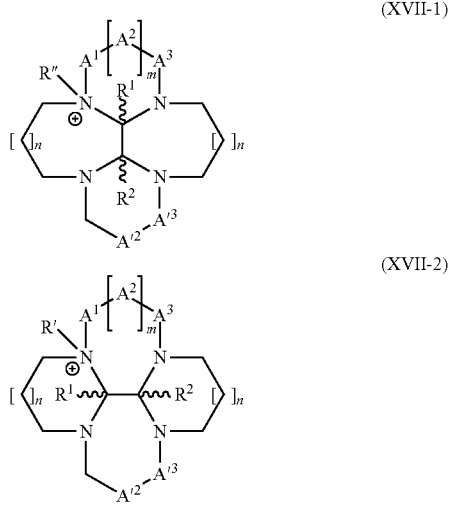

(XVII-1)

(XVII-2)

wherein: $A^1, A^2, A^3, A'^2, A'^3, R^1$ and $R^2$, m and n are as defined in the formula (I) or (II), the groups R", which are identical or different, are as defined in the formula (XIII).

The compound having formula (XVII) can be used as a starting reagent to prepare a compound known as a C-functionalized and N-di-functionalized side-bridge compound having the following formula (XVII'), one of its salts, solvates or their mixture:

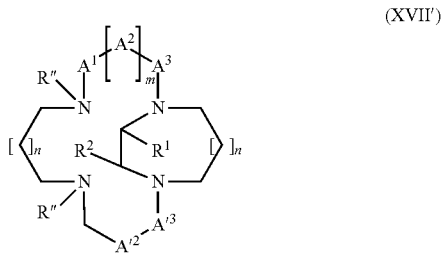

(XVII')

wherein: $A^1, A^2, A^3, A'^2, A'^3, R^1$ and $R^2$, m and n are as defined in the formula (I) or (II), the groups R", which are identical or different, are as defined in the formula (XIII).

The compound (XVII') can be prepared by implementing the steps (i) and (ii) as described here above for example, and then by implementing the following step (iii):
(iii) substituting the non-substituted secondary amine of the tetranitrogen cycle of the compound having formula (XVII) by the group R" as defined in the formula (XIII), for example by means of an electrophilic agent R"Q, Q being a leaving group as defined here above.

The term "side bridge" is understood to mean that the cyclic compound possesses a bridge structure (ethylene bridge) between two constituent adjacent nitrogen atoms of the tetranitrogen cycle.

The term "constituent adjacent nitrogen atoms of the tetranitrogen cycle" is understood to mean that the two nitrogen atoms are bonded by a chain of carbon atoms which are constituent of the tetranitrogen cycle, not interrupted by a nitrogen atom.

Figure 1 gives a glimpse of some of the different methods according to the invention.

In all these variants listed here above, the compound having formula (I) and/or (II) that are made to react can be obtained by means of one of the two main methods of the preparation according to the invention described here above, i.e. either on the basis of two diamines or on the basis of a tetramine as defined further above.

The C-functionalized bisaminal cyclic compounds of the invention and the compounds obtained from such compounds as described here above can be in the form of salts or solvates.

The salts can be chosen from amongst the salts formed with an inorganic acid such as hydrochloric acid, sulphuric acid, phosphoric acid, nitric acid, carbonic acid, boric acid, sulfamic acid, hydrobromic acid; or else salts formed with an organic acid, such as acetic acid, propionic acid, butyric acid, tartaric acid, maleic acid, hydroxymaleic acid, fumaric acid, maleic acid, citric acid, lactic acid, mucic acid, gluconic acid, benzoic acid, succinic acid, oxalic acid, phenylacetic acid, methanesulfonic acid, toluenesulfonic acid, benzenesulfonic acid, salicylic acid, sulfanilic acid, aspartic acid, glutamic acid, edetic acid, stearic acid, palmitic acid, oleic acid, lauric acid, panthotenic acid, tannic acid, ascorbic acid and valeric acid. When the compound according to the invention comprises an acid function, it can take the form of a salt with an organic or mineral base. Apart from cases where $R^1$ and $R^2$ of the above formulae both represent hydrogen atoms, salt or salts, if any, in these compounds are preferably salts formed with an organic base or mineral base.

Among all the C-functionalized and N-functionalized compounds described here above, the compounds preferred are those for which R represents a functional group having a coupling function, for example alcohol, and for which R" or R'" represent a functional group having a coordination function.

Owing to their chelating property and the capacity to be grafted onto a given support, the compounds obtained from C-functionalized bisaminal cyclic compounds according to the invention can be used in a wide variety of fields of applications such as catalysis, magnetism, materials, purification of liquids and gases, methods of analysis and the detection, medicine, especially nuclear medicine in particular as an imaging agent for position emission thermography (PET), ($\beta^+$ emitter: $^{64}$Cu, $^{68}$Ga . . . ) or in radioimmunotherapy (RIT) (emitter $\alpha$, $\beta^+$ or $\beta^-$: $^{212, 213}$Bi, $^{64}$Cu, $^{67}$Cu, . . . ), especially with respect to cancerous cells such as melanomas, neuroblastomas, cancerous cells of the prostate or the stomach.

The C-functionalized cyclic bisaminal compound according to the invention can thus be used to manufacture a metal chelating agent and/or a radionucleide (copper, bismuth or gallium).

In particular, the compound having formula (I) or (II), more particularly the compound having formula (III), can be used to manufacture a radiopharmaceutical (radioimmunotherapy (RIT)) or an imaging agent for position emission tomography (PET), especially as defined here above.

The following examples serve to illustrate the different objects of the invention.

EXAMPLES

1) Instrumentation

Nuclear Magnetic Resonance Spectrometery (NMR)
The NMR spectra were recorded by means of the following types of equipment:
BRUKER AMX 3 300 ($^1$H: 300.13 MHz; $^{13}$C: 75.47 MHz)
BRUKER DRX 500 ($^1$H: 500.13 MHz; $^{13}$C: 125.76 MHz)
The spectra were referenced by means of a deuterated solvent. The chemical shifts are indicated in ppm.
Infrared Spectroscopy (IR)
The infrared spectrum was obtained on a Perkin Elmer (Spectrum One) apparatus.
Mass Spectrometery (MS)
The measurements of the molecular masses was done by means of an Autoflex MALDI TOF III LRF200 CID spectrometer using dithranol or 2,5-dihydroxybenzoic acid (DHB) as a matrix.

Example 1

Preparation of C-Functionalized Glyoxal Cyclam Amides (1) and (2)

1) Cis-glyoxal cyclam amide C—CH$_2$CH$_2$OH (1)

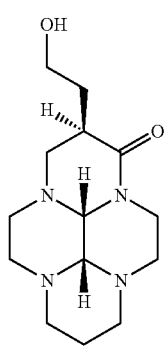

40 mL of a glyoxal solution in methanol, 40% by mass (31.20 mmol; 1.81 g) is added dropwise to a solution of 1,4,8,11-tetraazatetradecane (31.20 mmol; 5.00 g) in 100 mL of methanol at −5° C. Stirring is maintained for two hours. After returning to ambient temperature (25° C.), a solution of α-methylene-γ-butyrolactone (31.20 mmol; 3.50 g) in 40 mL of methanol is added dropwise to the reaction medium. The solution is stirred at 45° C. for seven days. After evaporation of the solvent, the mixture is recrystallised in acetronile. The compound (1) is obtained in the form of white crystals washed with diethyl ether (C$_{14}$H$_{24}$N$_4$O$_2$, M=280.19 g·mol$^{-1}$; 15.60 mmol; 4.37 g; yield 50%).

NMR $^1$H (300 MHz, 298K, CDCl$_3$, δ in ppm): 5.50 (s, 1H, OH); 4.45 (d, J=6.8 Hz, 1H, CH$_2$-α-N); 4.31 (s, 1H, CH); 3.38 (m, 1H, CH$_2$—OH); 3.36 (t, J=6.8 Hz, 1H, CH$_2$—OH); 3.35 (t, J=6.8 Hz, 1H, CH$_2$-α-N); 3.18 (s, 1H, CH); 3.09 (m, 2H, CH$_2$-α-N); 2.96 (m, 4H, CH$_2$-α-N); 2.76 (m, 3H, CH$_2$-α-N, CH-β-N); 2.53 (d, J=6.8 Hz, 1H, CH$_2$-α-N); 2.44 (d, J=6.8 Hz, 1H, CH$_2$-α-N); 2.25 (m, 1H, CH$_2$-α-N); 2.15 (m, 2H, CH$_2$-α-N, CH$_2$-β-N); 1.92 (m, 1H, CH$_2$-γ-N); 1.37 (d, J=8.5 Hz, 1H, CH$_2$-γ-N); 1.27 (d, J=8.5 Hz, 1H, CH$_2$-β-N).

NMR $^{13}$C (300 MHz, 298K, CDCl$_3$, δ in ppm): 173.1 (CO); 75.7 (CH); 70.6 (CH); 61.7 (CH$_2$—OH); 55.6 (CH$_2$-α-N); 54.9 (CH$_2$-α-N); 53.0 (CH$_2$-α-N); 52.7 (CH$_2$-α-N); 44.1 (CH$_2$-α-N); 43.6 (CH$_2$-α-N); 40.3 (CH$_2$-α-N); 35.4 (CH-β-N); 31.7 (CH$_2$-γ-N); 19.3 (CH$_2$-β-N).

IR: $\upsilon_{amide}$=1616 cm$^{-1}$.
Elemental analysis: Calculated=C, 59.98; H, 8.63; N, 19.98. Found=C, 59.91; H, 8.71; N, 20.09.
Mass spectrometery (MALDI-TOF): m/z=281.23 g·mol$^{-1}$ (M+1)$^+$ 2) Cis-glyoxal cyclam amide C—CH$_2$COOCH$_3$ (2)

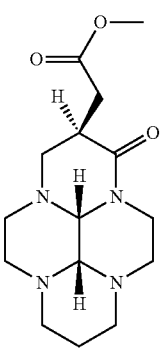

40 mL of a solution of glyoxal in methanol, 40% by mass (24.96 mmol; 1.40 g) are added dropwise to a solution of 1,4,8,11-tetraazatetradecane (24.96 mmol; 4.00 g) in 100 mL of methanol at −5° C. Stirring is maintained for two hours. After return to ambient temperature (25° C.), a solution of dimethylitaconate (24.96 mmol; 3.50 g) in 40 mL of methanol is added dropwise to the reaction medium. The solution is stirred at 45° C. for 14 days. The mixture is dried and then purified by silica gel chromatography using a CHCl$_3$/CH$_3$OH (in proportions of 100/0-94/6 volume per unit volume (v/v)) as an eluent. The compound (2) takes the form of a yellow oil (C$_{15}$H$_{24}$N$_4$O$_3$, M=308.18 gmol$^{-1}$; 14.73 mmol; 4.54 g; yield 59%).

NMR $^{13}$C (300 MHz, 298K, CDCl$_3$, δ in ppm): 172.5 (CO-amide); 170.8 (CO-ester); 76.0 (CH); 71.0 (CH); [55.9; 53.9; 53.2; 53.0; 44.5; 43.9; 40.5] (CH$_2$-α-N); 51.7 (—OCH$_3$); [33.2; 32.5] (CH-β-N; CH$_2$-γ-N); 19.6 (CH$_2$-β-N).

IR: $\upsilon_{amide}$=1616 cm$^{-1}$.
Elemental analysis: Calculated=C, 58.42; H, 7.84; N, 18.17. Found=C, 58.71; H, 8.01; N, 18.19.
Mass spectrometry (MALDI-TOF): m/z=309.21 gmol$^{-1}$ (M+1)$^+$.

Example 2

Synthesis of a N-di-trans-functionalized C-functionalized cyclam (8)

1) Cis-glyoxal cyclam C—CH$_2$CH$_2$OH (3)

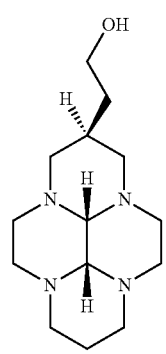

To an aqueous solution of the compound (1) (3.00 g; 10.71 mmol) sodium borohydride (107.10 mmol; 4.05 g) is added slowly, at an ambient temperature. The mixture is stirred for 18 hours. After evaporation of the solvent, the boron salts are precipitated by the addition of dichloromethane. The mixture is filtered and the solvent is evaporated to obtain the compound (3) in the form of a yellow oil ($C_{14}H_{26}N_4O$, M=266.38 gmol$^{-1}$ 2.71 g; 10.18 mmol; yield 95%).

NMR $^1$H (300 MHz, 298K, CDCl$_3$, δ in ppm): 3.64 (m, 2H, CH$_2$—OH); 3.51 (dt, J=20 Hz, J=3.4 Hz, 2H, CH$_2$-α-N); 3.10 (s, 1H, CH); 2.99 (m, 2H, CH, CH$_2$-α-N); 2.94 (m, 4H, CH$_2$-α-N); 2.78 (d, J=3.4 Hz, 1H, OH); 2.73 (m, 2H, CH$_2$-α-N); 2.57 (t, J=3.4 Hz, 2H, CH$_2$-α-N); 2.32 (m, 3H, CH$_2$-α-N, CH$_2$-γ-N); 2.22 (m, 2H, CH$_2$-α-N, CH$_2$-β-N); 2.14 (m, 1H, CH$_2$-α-N); 1.70 (m, 1H, CH$_2$-α-N); 1.34 (q, J=3.4 Hz, 2H, CH-β-N, CH$_2$-γ-N); 1.22 (m, 1H, CH$_2$-β-N).

NMR $^{13}$C (300 MHz, 298K, CDCl$_3$, δ in ppm): 77.3 (CH×2); 62.3 (CH$_2$-α-N); 60.4 (CH$_2$—OH); 58.8 (CH$_2$-α-N); 56.1 (CH$_2$-α-N×2); 54.5 (CH$_2$-α-N); 52.6 (CH$_2$-α-N); 45.8 (CH$_2$-α-N); 44.8 (CH$_2$-α-N); 34.9 (CH-β-N); 28.2 (CH$_2$-γ-N); 19.7 (CH$_2$-β-N).

Elemental analysis: Calculated=C, 62.12; H, 9.84; N, 21.03. Found.e=C, 61.89; H, 9.92; N, 21.19.

Mass spectrometry (MALDI-TOF): m/z=267.41 gmol$^{-1}$ (M+1)$^+$.

2) N-trans-dibenzyl cis-glyoxal cyclam C—CH$_2$CH$_7$OH (4)

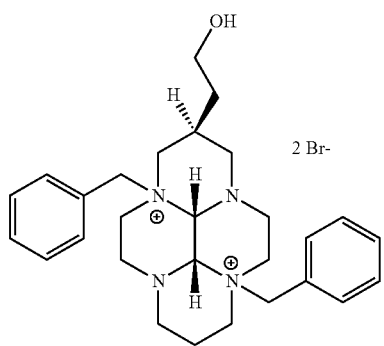

A solution of benzyl bromide (13.99 mmol; 2.38 g) in 20 mL of distilled acetonitrile is added dropwise to a solution of the derivate (3) (1.38 g; 5.18 mmol) in 45 mL of distilled acetonitrile. The mixture is stirred at ambient temperature for seven days. The solution is filtered to obtain the compound (4) in the form of a white powder ($C_{28}H_{40}Br_2N_4O$, M=606.16 gmol$^{-1}$; 1.88 g, yield 60%).

NMR $^1$H (300 MHz, 298K, CDCl$_3$, δ in ppm): 7.63 (m, 10H, H—Ar); 5.33 (t, J=7.7 Hz, 2H, CH$_2$—Ar); 5.13 (d, J=7.7 Hz, 2H, CH); 4.78 (m, 2H, CH$_2$—Ar); 4.46 (q, J=7.7 Hz, 2H, CH$_2$-α-N); 3.78 (t, J=7.7 Hz, 1H, CH$_2$-α-N); 3.64 (m, 4H, OH, CH$_2$-α-N, CH$_2$—OH); 3.50 (m, 5H, CH$_2$-α-N); 3.32 (m, 4H, CH$_2$-α-N); 2.87 (t, J=7.7 Hz, 1H, CH$_2$-α-N); 2.60 (m, 2H, CH$_2$-α-N, CH-β-N); 2.33 (m, 1H, CH$_2$-β-N); 2.29 (m, 1H, CH$_2$-γ-N); 1.95 (d, J=7.7 Hz, 2H, CH$_2$-β-N, CH$_2$-γ-N); 1.56 (m, 1H, CH$_2$-α-N).

NMR $^{13}$C (300 MHz, 298K, CDCl$_3$, δ in ppm): 136.1 (CH—Ar×4); 134.4 (CH—Ar×4); 132.4 (CH—Ar×2); 127.6 (C—Ar×2); 79.8 (CH); 79.5 (CH); 67.3 (CH$_2$-α-N); 65.3 (CH$_2$-α-N); 65.3 (CH$_2$-α-N); 63.5 (CH$_2$-α-N); 61.2 (CH$_2$—OH); 59.7 (CH$_2$-α-N); 54.1 (CH$_2$-α-N); 49.7 (CH$_2$-α-N); 49.6 (CH$_2$-α-N×2); 49.0 (CH$_2$-α-N); 35.0 (CH$_2$-γ-N); 28.6 (CH-β-N); 20.9 (CH$_2$-β-N).

Elemental analysis: Calculated=C, 53.68; H, 6.76; N, 8.94. Found=C, 53.79; H, 6.81; N, 9.21 ($C_{28}H_{40}Br_2N_4O$, $H_2O$)

Mass spectrometry (MALDI-TOF): m/z=448.33 gmol$^{-1}$ (M)$^+$.

5) N-trans-dibenzyl cyclam C—CH$_2$CH$_2$OH (5)

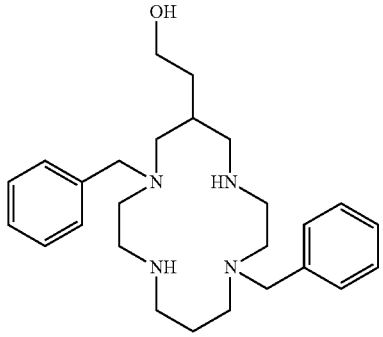

The compound (4) (1.20 g; 1.98 mmol) is dissolved in 6.0 mL of hydrazine hydrate. The mixture is brought to reflux for four hours. After cooling of the mixture, the hydrazine hydrate is eliminated. After the adding of 15 mL of distilled water, the product is extracted with chloroform (3×30 mL). The organic phases collected are dried over magnesium sulfate, filtered and then evaporated. The compound (5) obtained is a yellow oil ($C_{26}H_{40}N_4O$, M=424.32 gmol$^{-1}$; 760 mg, 1.79 mmol; yield 90%).

NMR $^1$H (300 MHz, 298K, CDCl$_3$, δ in ppm): 7.25 (m, 10H, H—Ar); 3.94 (d, J=7.9 Hz, 1H, CH$_2$-α-N); 3.72 (d, J=7.9 Hz, 2H, CH$_2$—Ar); 3.62 (m, 5H, CH$_2$—Ar, CH$_2$—OH, OH); 3.54 (m, 1H, CH$_2$-γ-N); 3.35 (d, J=7.9 Hz, 1H, CH$_2$-α-N); 2.92 (m, 1H, CH$_2$-α-N); 2.85 (m, 3H, CH$_2$-α-N); 2.65 (m, 3H, CH$_2$-α-N); 2.53 (m, 3H, CH$_2$-α-N); 2.45 (m, 1H, CH$_2$-α-N); 2.31 (d, J=7.9 Hz, 1H, CH$_2$-α-N); 2.16 (s, 3H, CH-β-N, NH); 2.11 (d, J=7.9 Hz, 1H, CH$_2$-α-N); 1.83 (m, 1H, CH$_2$-β-N); 1.72 (m, 1H, CH$_2$-β-N); 1.63 (m, 1H, CH$_2$-α-N); 1.50 (m, 1H, CH$_2$-γ-N).

NMR $^{13}$C (300 MHz, 298K, CDCl$_3$, δ in ppm): 137.6 (C—Ar×2); 129.4 (CH—Ar×4); 128.3 (CH—Ar×4); 127.2 (CH—Ar×2); 59.1 (CH$_2$—OH, CH$_2$-α-N); 57.9 (CH$_2$-α-N×2); 54.0 (CH$_2$-α-N); 52.5 (CH$_2$-α-N); 51.7 (CH$_2$-α-N); 51.2 (CH$_2$-α-N); 49.4 (CH$_2$-α-N); 47.8 (CH$_2$-α-N); 46.9 (CH$_2$-α-N); 36.4 (CH$_2$-γ-N); 31.0 (CH-β-N); 26.3 (CH$_2$-β-N)

Elemental analysis: Calculated=C, 73.54; H, 9.49; N, 13.19. Found=C, 73.69; H, 9.19; N, 13.02.

Mass spectrometry (MALDI-TOF): m/z=425.32 gmol$^{-1}$ (M+1)$^+$.

6) N-trans-dibenzyl N-trans-diacetate-tert-butyl cyclam C—CH$_2$CH$_7$OH (6)

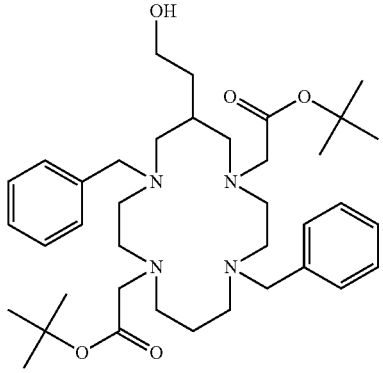

A solution of tert-butyl bromoacetate (2.02 g; 10.36 mmol) in 45 mL of distilled acetonitril is added dropwise to a solution of the compound (5) (2.00 g; 4.71 mmol) and of potassium carbonate (2.60 g; 18.84 mmol) in 80 mL of distilled acetonitril preliminarily heated to 40° C. The solution is stirred for six days at 40° C. and then filtered on celite. After evaporation of the solvent, the brown oil obtained is solubilized in 15 mL of distilled water. A solution of hydrochloric acid 3M (mol/L) is added up to pH=2. After extraction of the impurities with hexane (5×30 mL), the aqueous phase is made basic up to pH=12 by addition of a solution of sodium hydroxide 4M. The product is extracted with chloroform (5×60 mL); the collected organic phases are dried over magnesium sulfate and then evaporated to give the compound (6) in the form of a yellow oil ($C_{38}H_{60}N_4O_5$, M=652.46; 1.94 g, 2.97 mmol, yield 63%).

NMR $^{13}C$ (300 MHz, 298K, $CDCl_3$, δ in ppm): [170.6; 170.4] (CO); [139.5; 138.2; 129.7; 128.9; 128.3; 128.1; 127.2; 126.8] (CH—Ar, C—Ar×); [80.7; 80.6] ($C(CH_3)_3$); [61.3; 60.9; 60.8; 60.7; 60.0; 59.2; 57.4; 56.7; 51.6; 51.1; 51.0; 50.8; 48.9] ($CH_2$—OH, $CH_2$-α-N); [37.8; 35.7](CH-β-N, $CH_2$-γ-N); 28.0 ($C(CH_3)_3$×2); 24.9 ($CH_2$-β-N).

Mass spectrometry (MALDI-TOF): m/z=653.49 gmol$^{-1}$ (M+1)$^+$.

7) N-trans-diacetate tert-butyl cyclam C—$CH_2CH_2OH$ (7)

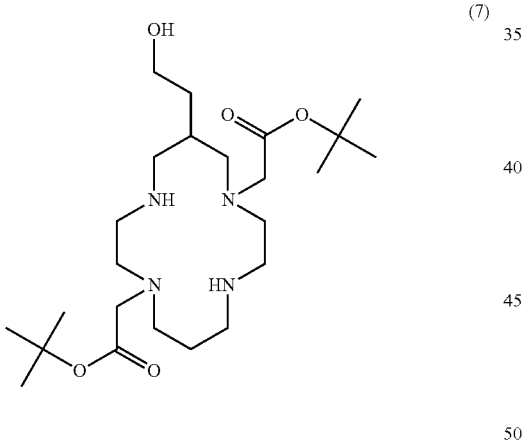

(7)

The compound (6) (930 mg; 1.43 mmol) is dissolved in 60 mL of a solution of 200 mg of palladium on activated carbon (activated Pd/C) 10% by mass in glacial acetic acid, in a dihydrogen atmosphere. The mixture is stirred for four days. The product obtained takes the form of a brown oil ($C_{24}H_{48}N_4O_5$, M=472.36 gmol$^{-1}$; 392 mg, 0.83 mmol; yield 58%).

NMR $^{13}C$ (300 MHz, 298K, $CDCl_3$, δ in ppm): [170.4; 170.3] (CO); 80.6 ($C(CH_3)_3$×2); [59.3; 57.8; 55.8; 54.7; 54.3; 53.4; 52.7; 52.4; 49.3; 47.6; 46.7] ($CH_2$—OH, $CH_2$-α-N); [35.9; 34.1] (CH-β-N, $CH_2$-α-N); 28.0 ($C(CH_3)_3$×2); 26.1 ($CH_2$-β-N).

Mass spectrometry (MALDI-TOF): m/z=472.40 gmol$^{-1}$ (M+1)$^+$.

8) N-trans-diacetate cyclam C—$CH_2CH_2OH$, 4.$CF_3COOH$ (8)

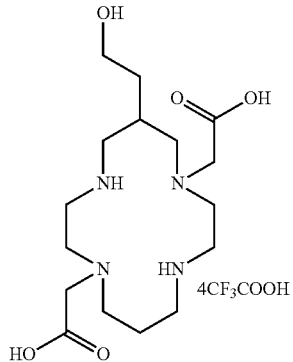

(8)

The compound (7) (392 mg; 0.83 mmol) is dissolved in 10 mL of trifluoroacetic acid. The solution is stirred for 18 hours at ambient temperature. The solvent is evaporated. The compound is obtained quantitatively in the form of a brown solid ($C_{24}H_{36}F_{12}N_4O_{13}$, M=816.54 gmol$^{-1}$; 678 mg, 0.83 mmol; quantitative).

NMR $^{13}C$ (300 MHz, 298K, $D_2O$, δ in ppm): [178.1; 177.0] (CO); [67.6; 65.4; 60.6; 59.3; 58.3; 56.8; 55.3; 51.9; 51.3; 50.7; 47.5] ($CH_2$—OH, $CH_2$-α-N); [34.9; 32.4] (CH-β-N, $CH_2$-α-N); 24.6 ($CH_2$-β-N).

Mass spectrometry (MALDI-TOF): m/z=360.51 gmol$^{-1}$ (M+1)$^+$.

Example 3

Synthesis of a C-Functionalized Cyclam-"Cross Bridge" (10)

1) N-trans-dibenzyl cross-bridged cyclam C—$CH_2CH_2OH$ (9)

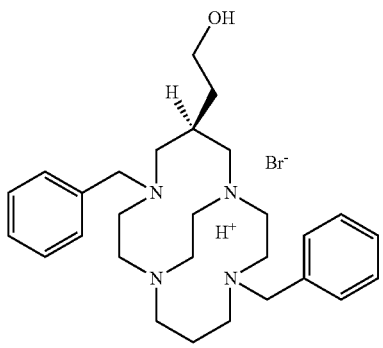

(9)

Sodium borohydride (998 mg; 26.40 mmol) is added slowly to 50 mL of an ethanol solution 95% by mass of the compound (4) (1.00 g; 1.65 mmol). The mixture is stirred for 12 days at ambient temperature (25° C.). After evaporation of the solvent, the boron salts are precipitated by the addition of dichloromethane. The mixture is filtered and the solvent is evaporated to obtain the compound in the form of a yellow oil ($C_{28}H_{43}BrN_4O$, M=530.26 g·mol$^{-1}$; 744 mg; 1.40 mmol; yield 85%).

NMR $^1H$ (300 MHz, 298K, $CDCl_3$, δ in ppm): 10.29 (s, 1H, NH); 7.26 (m, 10H, H—Ar); 3.73 (m, 5H, $CH_2$-α-N, $CH_2$—Ar×2); 3.66 (m, 4H, OH, $CH_2$-α-N, $CH_2$—OH); 3.49 (d, J=7.1 Hz, 5H, $CH_2$-α-N×4); 3.31 (m, 2H, $CH_2$-α-N×2); 3.13 (m, 3H, $CH_2$-α-N×3); 3.00 (m, 3H, $CH_2$-α-N×2); 2.76 (m, 4H, CH$_2$-α-N×3, CH-β-N); 2.42 (m, 2H, CH$_2$-α-N, CH$_2$-γ-N); 1.96 (s, 1H, CH$_2$-β-N); 1.59 (m, 1H, CH$_2$-α-N); 1.36 (m, 1H, CH$_2$-γ-N); 1.18 (m, 1H, CH$_2$-β-N).

NMR $^{13}$C (300 MHz, 325K, CDCl$_3$): δ (ppm) [136.1; 134.1; 130.2; 129.7; 128.4; 128.3; 127.6; 127.4] (CH—Ar, C—Ar×); 62.3 (CH$_2$—OH); 59.9 (CH$_2$-α-N); 58.1 (CH$_2$-α-N); 57.5 (CH$_2$-α-N×2); 55.5 (CH$_2$-α-N×2); 54.0 (CH$_2$-α-N×2); 51.8 (CH$_2$-α-N); 51.3 (CH$_2$-α-N); 50.6 (CH$_2$-α-N×2); 33.3 (CH$_2$-γ-N); 29.8 (CH-β-N); 24.6 (CH$_2$-β-N).

Mass spectrometry (MALDI-TOF): m/z=450.34 gmol$^{-1}$ (M+1)$^+$.

Elemental analysis: Calculated=C, 63.39; H, 7.98; N, 10.56. Found=C, 63.67; H, 8.11; N, 10.33.

2) Cross-bridged cyclam C—CH$_2$CH$_2$OH (10)

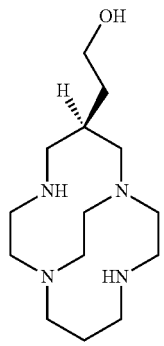

(10)

The mode of operation is the one used for the synthesis of the compound (7). The reagents brought into play are: a) compound (9) (700 mg; 1.32 mmol); b) Pd/C, 10% (140 mg). The mode of operation diverges by the daily addition of 50 mg of Pd/C to the reaction mixture. The expected compound is a yellow oil (C$_{14}$H$_{30}$N$_4$O, M=270.24 g·mol$^{-1}$; 357 mg; 1.32 mmol; yield 48%).

NMR $^{13}$C (300 MHz, 298K, CDCl$_3$, δ in ppm): 62.7 (CH$_2$—OH); 59.4 (CH$_2$-α-N); 59.1 (CH$_2$-α-N); 58.3 (CH$_2$-α-N×2); 55.3 (CH$_2$-α-N×2); 54.4 (CH$_2$-α-N×2); 52.0 (CH$_2$-α-N); 51.3 (CH$_2$-α-N); 50.6 (CH$_2$-α-N×2); 33.8 (CH$_2$-γ-N); 30.0 (CH-β-N); 24.9 (CH$_2$-β-N).

Mass spectrometry (MALDI-TOF): m/z=271.26 gmol$^{-1}$ (M+1)$^+$.

Example 4

N-Monofunctionalized and C-Functionalized Cyclam (13) and C-Functionalized Cyclam Amide (13')

1) Preparation of N-monobenzyl cyclam-amide C—CH$_2$CH$_2$OH (12)

Cis-glyoxal N-monobenzyl cyclam amide C—CH$_2$CH$_2$OH (11)

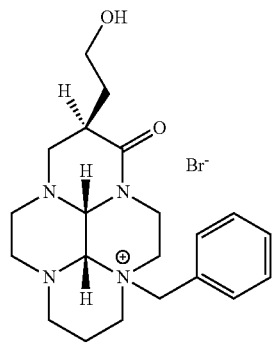

(11)

A solution of benzyl bromide (1.46 g; 8.56 mmol) in 20 mL of distilled acetonitril is added dropwise to a solution of cyclam-cis-glyoxal amide C—CH$_2$CH$_2$OH (1) (2.00 g; 7.13 mmol) in 80 mL of distilled acetonitrile preliminarily heated to 40° C. Stirring is maintained for four days. After evaporation of the solvent, 25 mL of distilled water is added to the yellow solid obtained. The excess benzyl bromide is extracted with hexane (3×30 mL). The aqueous phase is evaporated to obtain the expected compound in the form of a yellow solid (C$_{21}$H$_{31}$N$_4$BrO$_2$, M=451.16 g·mol$^{-1}$; 3.15 g; 6.98 mmol; yield 98%).

NMR $^1$H (300 MHz, 298K, D$_2$O, δ in ppm): 7.64 (d, J=7.7 Hz, 2H, H—Ar); 7.31 (m, 3H, H—Ar); 5.96 (s, 1H, CH); 5.76 (d, J=7.7 Hz, 1H, CH$_2$—Ar); 5.59 (d, J=7.7 Hz, 1H, CH$_2$—Ar); 4.59 (s, 1H, CH); 4.56 (m, 1H, CH$_2$-α-N); 4.33 (m, 1H, OH); 4.24 (m, 2H, CH$_2$-α-N×2); 3.97 (m, 1H, CH$_2$-α-N); 3.77 (m, 2H, CH$_2$—OH); 3.59 (m, 1H, CH$_2$-α-N); 3.43 (m, 1H, CH$_2$-α-N); 3.31 (m, 1H, CH$_2$-α-N); 3.18 (m, 1H, CH$_2$-α-N); 2.94 (m, 1H, CH-β-N); 2.87 (m, 2H, CH$_2$-α-N×2); 2.71 (m, 1H, CH$_2$-α-N); 2.48 (m, 1H, CH$_2$-α-N); 2.08 (m, 2H, CH$_2$-β-N, CH$_2$-γ-N); 1.79 (m, 2H, CH$_2$-β-N, CH$_2$-γ-N).

NMR $^{13}$C (300 MHz, 298K, D$_2$O, δ in ppm): 177.6 (CO), 128.0 (C—Ar); 136.2 (CH—Ar×2); 132.5 (CH—Ar×2); 134.3 (CH—Ar); 83.4 (CH); 68.0 (CH); 65.9 (CH$_2$—Ar); 64.3 (CH$_2$-α-N); 62.6 (CH$_2$—OH); [55.8; 55.2; 54.4; 50.0; 45.5; 38.8] (CH$_2$-α-N); 35.8 (CH-β-N); 34.0 (CH$_2$-γ-N); 20.6 (CH$_2$-β-N).

Mass spectrometry (MALDI-TOF): m/z=371.26 gmol$^{-1}$ (M)$^+$.

IR: $\upsilon_{amide}$=1616 cm$^{-1}$.

Elemental analysis: Calculated=C, 55.88; H, 6.92; N, 12.41. Found=C, 55.68; H, 6.98; N, 12.09.

N-monobenzyle Cyclam-amide C—CH$_2$CH$_2$OH (12)

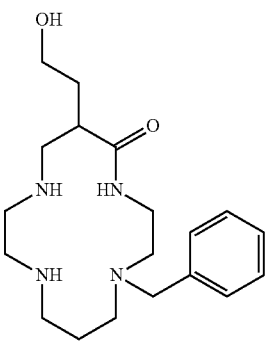

(12)

The mode of operation is the one used for the synthesis of the compound 5. The reagents brought into play are: a) compound (11) (550 mg; 1.22 mmol); b) hydrazine hydrate (3 mL). The product obtained takes the form of a colorless oil (C$_{19}$H$_{32}$N$_4$O$_2$, M=348.25 g·mol$^{-1}$; 327 mg; 0.94 mmol; yield 77%).

NMR $^1$H (300 MHz, 298K, CDCl$_3$, δ in ppm): δ (ppm) 7.26 (m, 5H, H—Ar); 3.86 (d, J=16 Hz, 1H, CH$_2$—Ar); 3.55 (m, 2H, CH$_2$—OH); 3.12 (d, J=16 Hz, 1H, CH$_2$-Ph); 3.05 (m, 1H, CH-β-N); 2.20-2.90 (m, 14H, CH$_2$-α-N); 2.00 (m, 1H, CH$_2$-β-N); 1.73 (m, 1H, CH$_2$-γ-N); 1.65 (m, 1H, CH$_2$-γ-N); 1.55 (m, 1H, CH$_2$-β-N).

NMR $^{13}$C (300 MHz, 298K, CDCl$_3$, δ in ppm): 175.7 (CO); [138.5; 129.5; 128.0; 126.9] (C—Ar, CH—Ar); 59.7 ($_c$H$_2$—OH); 57.7 (CH$_2$—Ar); [54.6; 52.8; 50.9; 50.4; 49.3; 47.4; 42.5]; 35.8 (CH$_2$-γ-N); 33.1 (CH-β-N); 25.2 (CH$_2$-β-N).

Mass spectrometry (MALDI-TOF): m/z=349.27 gmol$^{-1}$ (M+1)$^+$.
IR: $\upsilon_{amide}$=1616 cm$^{-1}$.
Elemental analysis: Calculated=C, 65.48; H, 9.26; N, 16.08. Found=C, 65.69; H, 9.44; N, 16.11.

2) Preparation of N-monobenzyl cyclam C—CH$_2$CH$_2$OH (13)

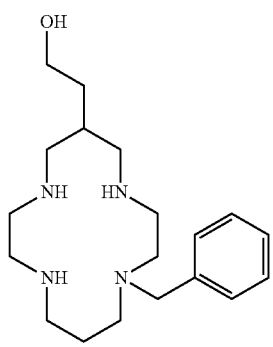

(13)

In a nitrogen atmosphere, 2.4 ml of a solution of borane-tetrahydrofuran complex (BH$_3$.THF; 1M; 2.40 mmol) is added to a solution of monobenzyl cyclam-amide (12) (140 mg; 0.40 mmol) in 30 mL of distilled THF. The reaction medium is brought to reflux for two days. 30 mL of distilled water is added to the mixture, cooled to 0° C., to destroy the excess BH$_3$-THF complex. After evaporation of the solvent, 25 mL of a solution of hydrochloric acid 3M is added to the white solid obtained. The solution is taken to reflux for one hour and then cooled to 0° C. Sodium hydroxide pellets are added up to pH=12. The product is extracted with chloroform (3×30 mL); the collected organic phases are dried over magnesium sulfate and then evaporated to give the expected compound in the form of a colorless oil (C$_{19}$H$_{34}$N$_4$O, M=334.27 g·mol$^{-1}$; 87 mg; 0.26 mmol; yield 65%).

NMR $^{13}$C (300 MHz, 298K, CDCl$_3$, δ in ppm): [138.7; 129.4; 128.3; 127.2](C—Ar, CH—Ar); [59.3; 57.9; 53.5; 52.8 (×2); 52.6; 48.6; 48.5; 47.8; 46.6] (CH$_2$—OH, CH$_2$-α-N); [35.5; 35.3](CH-β-N, CH$_2$-γ-N); 26.2 (CH$_2$-β-N).

Mass spectrometry (MALDI-TOF): m/z=335.29 gmol$^{-1}$ (M+1)$^+$.

3) Preparation of cyclam-amide N-monobenzyl C—CH$_2$CH$_2$OH (13')

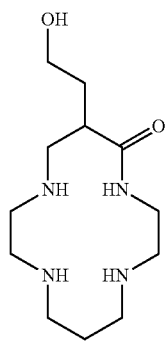

(13')

The mode of operation is the one used for the synthesis of the compound (7). The reagents brought into play are: a) compound (12) (700 mg; 2.01 mmol); b) Pd/C, 10% (140 mg). The expected compound is a yellow oil (C$_{12}$H$_{26}$N$_4$O$_2$, M=258.21 gmol$^{-1}$; 415 mg; 1.61 mmol; yield 80%).

NMR $^{13}$C (300 MHz, 298K, CDCl$_3$, δ in ppm): 176.1 (CO); 59.6 (CH$_2$—OH); [51.3; 51.1; 50.7; 50.1; 49.2; 47.1; 42.3]; 35.5 (CH$_2$-γ-N); 33.9 (CH-β-N); 25.7 (CH$_2$-β-N).

Mass spectrometry (MALDI-TOF): m/z=259.22 gmol$^{-1}$ (M+1)$^+$.
IR: $\upsilon_{amide}$=1616 cm$^{-1}$.

Example 7

N- and C-Functionalized Side-Bridged Cyclam

1) Preparation of N-monobenzyl side-bridged cyclam C—CH$_2$CH$_2$OH (14)

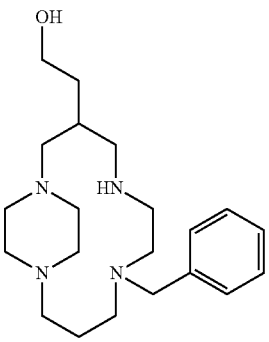

(14)

A solution of (11) (205.90 mg; 0.55 mmol) in distilled water is added slowly and at low temperature to sodium borohydride (333.00 mg; 8.80 mmol). The mixture is stirred and taken to reflux for five hours. After evaporation of the solvent, the product is extracted several times with chloroform and then filtered. The colorless oil obtained is purified by silica gel chromatography (C$_{21}$H$_{36}$N$_4$O, M=360.54 g·mol$^{-1}$; 140 mg; 0.31 mmol; yield 71%).

NMR $^{13}$C (300 MHz, 298K, CDCl$_3$, δ in ppm): [136.6; 125.9; 125.1; 123.8](C—Ar, CH—Ar); [64.2; 60.1; 57.6; 56.5; 53.7; 53.1; 51.1 (×2, pont); 50.4 (×2 pont); 49.4; 36.4] (CH$_2$—OH, CH$_2$-α-N); [33.1; 31.6](CH-β-N, CH$_2$-γ-N); 21.3 (CH$_2$-β-N).

Mass spectrometry (MALDI-TOF): m/z=361.62 gmol$^{-1}$ (M+1)$^+$.

Example 8

C-Functionalized Cyclam

1) Preparation of Cis-butanedione cyclam-amide C—CH$_2$COOCH$_3$ (15)

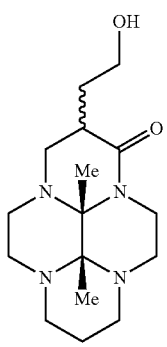

(15)

25 ml of a solution of α-methylene-γ-butyrolactone (1.07 g; 9.52 mmol) is added dropwise to a solution of 2,3,2-butanediome cis (2.00 g; 9.52 mmol) in 70 mL of methanol at 45° C. Stirring is maintained for 12 days at 45° C. The solvent is evaporated. 15 mL of a solution of sodium hydroxide 4M is added to the brown oil obtained. The solution is stirred for one night. The product is extracted with chloroform (3×30 mL). The compound (15) is a yellow oil ($C_{16}H_{28}N_4O_2$, M=308.22 g·mol$^{-1}$, 2.05 g; 6.66 mmol; yield 70%).

NMR $^{13}$C (300 MHz, 298K, CDCl$_3$, δ in ppm): 172.9 (CO); 75.5 (CH); 72.7 (CH); [60.4; 50.3; 48.8; 48.5; 46.2; 45.6; 43.1; 38.1] (CH$_2$—OH, CH$_2$-α-N); [32.9; 32.1] (CH-β-N, CH$_2$-γ-N); 24.5 (CH$_2$-β-N); 17.2 (CH$_3$); 10.5 (CH$_3$).

Mass spectrometry (MALDI-TOF): m/z=309.22 gmol$^{-1}$ (M+1)$^+$.

IR: $\upsilon_{amide}$=1616 cm$^{-1}$.

Elemental analysis: Calculated=C, 62.31; H, 9.15; N, 18.17. Found=C, 62.63; H, 9.18; N, 18.29.

2) Preparation of cyclam C—CH$_2$CH$_7$OH (16)

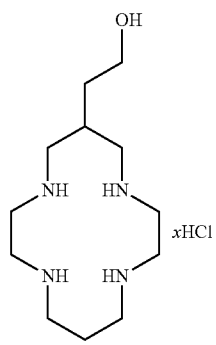

(16)

In a nitrogen atmosphere, 7.8 mL of a solution of borane-tetrahydrofurane complex (BH$_3$.THF; 1M; 7.80 mmol) is added slowly to a solution of the compound (15) (1.30 mmol, 400 mg) in 50 mL of distilled tetrahydrofurane. The mixture is stirred for 1.5 days in reflux under a nitrogen atmosphere. After cooling of the reaction medium to 0° C., 30 mL of distilled water is added in order to destroy the excess borohydride-tetrahydrofuran (BH$_3$.THF) complex. After evaporation of the mixture, 30 mL of a solution of hydrochloric acid 3M is added to the beige-colored solid obtained. The solution is taken to reflux for four hours. After evaporation of the solvents, the compound (16) is obtained in the form of a beige-colored solid ($C_{12}H_{52}N_4OCl_4$, M=388.13 gmol$^{-1}$; 403 mg; 1.04 mmol, yield 80%).

NMR $^{13}$C (300 MHz, 298K, D$_2$O, δ in ppm): 64.4 (CH$_2$—OH); 51.9 (CH$_2$-α-N×2); 44.8 (CH$_2$-α-N×2); 42.9 (CH$_2$-α-N×2); 42.3 (CH$_2$-α-N×2); 35.4 (CH-β-N); 31.7 (CH$_2$-γ-N); 30.7 (CH$_2$-β-N).

Mass spectrometry (MALDI-TOF): m/z=245.24 gmol$^{-1}$ (M+1)$^+$.

3) Preparation of N-tetra acetate tert-butyl cyclam C—CH$_2$CH$_7$OH (17)

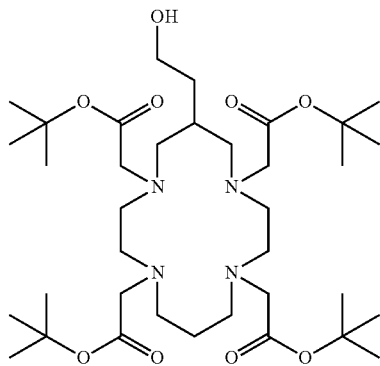

(17)

A solution of tert-butyl bromoacetate (796 mg; 4.08 mmol) in 45 mL of distilled acetonitril is added dropwise to a solution of cyclam C—CH$_2$CH$_2$OH (16) (250 mg; 1.02 mmol) and potassium carbonate (845 mg; 6.12 mmol) in 80 mL of distilled acetonitrile, preliminarily heated to 40° C. The solution is stirred for six days at 40° C. and then filtered on celite. After evaporation of the solvent, the yellow oil obtained is solubilized in chloroform and then washed in water (3×30 mL). The product is purified by silica gel chromatography with a mixture CHCl$_3$/CH$_3$OH (proportions in v/v; 100/0; 99/1; 98/2; 97/3; 96/4; 95/5) as an eluent. The compound is obtained in the form of a yellow oil ($C_{36}H_{68}N_4O_9$, M=700.50 g·mol$^{-1}$; 215 mg, 0.31 mmol; yield 60%).

NMR $^{13}$C (300 MHz, 298K, CDCl$_3$, δ in ppm): 170.9 (CO ester×2); 170.5 (CO ester×2); 81.2 (C(CH$_3$)$_3$×2); 80.9 (C(CH$_3$)$_3$×2); 61.3 (CH$_2$—OH); 60.5 (CH$_2$-α-N×2); 57.4 (CH$_2$-α-N×2); 56.9 (CH$_2$-α-N×2); 51.8 (CH$_2$-α-N×2); 51.1 (CH$_2$-α-N×2); 50.9 (CH$_2$-α-N×$^2$); 37.7 (CH-β-N); 36.0 (CH$_2$-γ-N); 28.3 (C(CH$_3$)$_3$×12); 25.4 (CH$_2$-β-N).

Mass spectrometry (MALDI-TOF): m/z=701.53 g·mol$^{-1}$ (M+1)$^+$.

4) Preparation of N-tetra acetate cyclam C—CH$_2$CH$_2$OH (18)

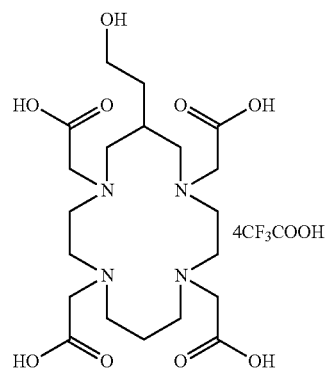

(18)

The compound (17) (100 mg; 0.14 mmol) is dissolved in 10 mL trifluoroacetic acid. The solution is stirred for 18 hours at ambient temperature. The solvent is evaporated. The compound (18) is obtained in the form of a brown solid ($C_{28}H_{40}F_{12}N_4O_{17}$, M=932.62 g·mol$^{-1}$; 130 mg; 0.14 mmol; quantitative).

NMR $^{13}C$ (300 MHz, 298K, $D_2O$, δ in ppm): 176.9 (CO acide×2); 178.5 (CO acide×2); 61.3 ($CH_2$—OH); 62.5 ($CH_2$-α-N×2); 58.4 ($CH_2$-α-N×2); 57.9 ($CH_2$-α-N×2); 53.8 ($CH_2$-α-N×2); 53.1 ($CH_2$-α-N×2); 51.9 ($CH_2$-α-N×2); 38.7 (CH-β-N); 37.0 ($CH_2$-γ-N); 26.4 ($CH_2$-β-N).

Mass spectrometry (MALDI-TOF): m/z=476.25 g·mol$^{-1}$ (M)$^+$. ($C_{20}H_{36}N_4O_9$)

The invention claimed is:

1. A compound according to formulae (I) or (II), wherein:

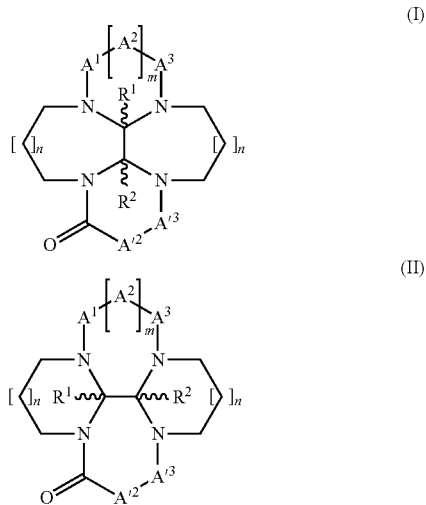

$R^1$ and $R^2$, identical or different, represent a hydrogen atom, a C1-C4 alkyl group, or, together with the carbon atoms of the bisaminal bridge to which they are linked, form a saturated or unsaturated, six-membered hydrocarbon cyclic group, wherein:

m and n, identical or different, are equal to 0 or to 1;

$A^1, A^2, A^3, A'^2, A'^3$, identical or different, are chosen from the groups $CH_2$, CHR and C=O; on condition that $A'^2$ or $A'^3$ designates a CHR group; and the group or groups R, identical or different, is:

a hydrocarbon group, saturated or unsaturated, straight or branched, cyclic or acyclic, comprising 1 to 30 carbon atoms, and comprising one or more heteroatoms selected from:

a group V, V being chosen from amongst a halogen, a nitrile, $NR^5R^6$, $NO_2$, $OR^7$, COX, NHCOX, —$CONR^5R^6$, $(O)_sPO(OR^8)(OR^9)$, s being an integer ranging from 0 to 1, X being a halogen or a group $OR^5$; $R^5, R^6, R^7, R^8$ and $R^9$ being chosen from amongst a hydrogen atom and a straight or branched, saturated or unsaturated $C_1$-$C_{30}$ alkyl group, a group W, wherein W is selected from a monocyclic, bicyclic or tricyclic, saturated or unsaturated cyclic hydrocarbon group with the cycle or cycles comprising 5 to 6 carbon atoms, and at least one of said cycle or cycles being capable of being substituted by one or more groups chosen amongst N-chlorosuccinimide, $P(C_6H_5)_2$, $P(O)(C_6H_5)_2$, $(CH_2)_p$ V, p being an integer ranging from 0 to 4 and/or being capable of forming, with one or more carbon atoms of the cycle, one or more ketone functions, a group Y, Y being a heterocyclic group, capable of being monocyclic, bicyclic or tricyclic, saturated or unsaturated, the cycle or cycles comprising five to six members, and at least one of them being capable of being substituted on at least one or more carbon atoms or heteroatoms by one or more groups chosen from amongst the groups V and W, a straight or branched, saturated or unsaturated, $C_1$-$C_{30}$, alkyl group substituted by one or more groups V and/or W, a trityl group; the heterocycle group being capable of forming, with one or more carbon atoms of the cycle, one or more ketone functions, a straight or branched saturated or unsaturated $C_1$-$C_{30}$ alkyl group substituted by one or more groups, V, W, and/or Y hydrophobic groups chosen from amongst saturated or unsaturated, straight or branched, cyclic or acylic hydrocarbon groups comprising at least one linear hydrocarbon chain having 8 to 30 carbon atoms, hydrophilic groups comprising at least one glycol ethylene group, tensioactive groups, fluorescent groups, ionic groups chosen from amongst organic groups of the guadinidium or arsenium type, groups bearing at least one protected or unprotected primary, protected or unprotected secondary or protected or unprotected tertiary amine function, groups bearing at least one alcohol function, groups bearing at least one alkene and/or alkyne function, groups bearing at least one amide function, groups bearing at least cyano, nitrile, $CF_3$ function, and groups bearing at least one acid, ester, aldehyde function.

2. The compound according to claim 1, wherein $A'^2$ designates a CHR group and, wherein R is:

a hydrocarbon group, saturated or unsaturated, straight or branched, cyclic or acyclic, comprising 1 to 30 carbon atoms, and comprising, one or more heteroatoms, a group V, V being chosen from amongst a halogen, a nitrile, $NR^5R^6$, $NO_2$, $OR^7$, COX, NHCOX, —$CONR^5R^6$, $(O)_sPO(OR^8)(OR^9)$, s being an integer ranging from 0 to 1, X being a halogen or a group $OR^5$; $R^5, R^6, R^7, R^8$ and $R^9$ being chosen from amongst a hydrogen atom and a straight or branched, saturated or unsaturated $C_1$-$C_{30}$ alkyl group, a group W, wherein W is selected from a monocyclic, bicyclic or tricyclic, saturated or unsaturated cyclic hydrocarbon with the cycle or cycles comprising 5 to 6 carbon atoms, and at least one of them being capable of being substituted by one or more groups chosen from amongst N-chlorosuccinimide, $P(C_6H_5)_2$, $P(O)(C_6H_5)_2$, $(CH_2)_p$, V, p being an integer ranging from 0 to 4 and/or being capable of forming, with one or more carbon atoms of the cycle, one or more ketone functions, a group Y, Y being a heterocyclic group, capable of being monocyclic, bicyclic or tricyclic, saturated or unsaturated, the cycle or cycles comprising five to six members, and at least one of them being capable of being substituted on at least one or more carbon atoms or heteroatoms by one or more groups chosen from amongst the groups V and W, a straight or branched, saturated or unsaturated $C_1$-$C_{30}$, alkyl group substituted by one or more groups V and/or W, a trityl group; the heterocycle group being capable of forming, with one or more carbon atoms of the cycle, one or more ketone functions, a straight or branched, saturated or unsaturated $C_1$-$C_{30}$ alkyl group substituted by one or more groups, V, W, and/or Y hydrophobic groups chosen from amongst saturated or unsaturated, straight or branched, cyclic or acyclic hydrocarbon groups comprising at least one linear hydrocarbon chain having 8 to 30 carbon atoms, hydrophilic groups comprising at least one glycol ethylene group, tensioactive groups, fluorescent groups, ionic groups chosen from amongst organic groups of the guadinidium or arsenium type, groups bearing at least one protected or unprotected primary, protected or unprotected secondary or protected or unprotected tertiary amine function, groups bearing at least one alcohol function, groups bearing at least one alkene and/or alkyne function, groups bearing at least one amide function, groups bearing at least cyano, nitrile, $CF_3$ function, and groups bearing at least one acid, ester, aldehyde function.

3. The compound according to claim 1, wherein one of its salts or solvates is formula (III):

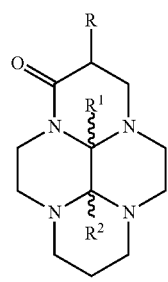
(III)

wherein $R^1$ and $R^2$ are as defined in the claim 1;

R is a group $(CH_2)_lX$ with l as an integer equal to zero or one, X being a group chosen from among a halogen atom, a hydroxyl, $CH_2OH$, $COOH$, $COOCH_3$, $COOC_2H_5$.

4. A method for preparing a compound of claim 1, comprising:

a step during which a tetramine having formula (VII) is made to react

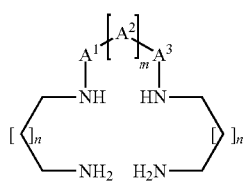
(VII)

wherein: $A^1$, $A^2$, $A^3$ are chosen from amongst from the groups $CH_2$, CHR and C=O, m and n, identical or different, are equal to 0 or 1, with a dicarbonyl compound having formula (IV):

(IV)

wherein: $R^1$ and $R^2$, identical or different, represent a hydrogen atom, a $C_1$-$C_4$ alkyl group, or together form, with the carbon atoms to which they are linked, a saturated or unsaturated cyclic hydrocarbon group with six carbon atoms to form a bisaminal intermediate having formula (VIII) or (IX) or a mixture of these compounds:

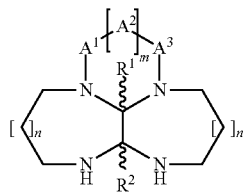
(VIII)

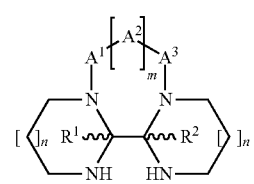
(IX)

formulae (VIII) and (IX) wherein: $A^1$, $A^2$, $A^3$, m, n are as defined in the formula (VII) and $R^1$ and $R^2$ are as defined in the formula (IV), then a step during which the intermediate or intermediates obtained are made to react with a cyclizing agent meeting the formula (VI):

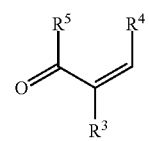
(VI)

wherein:

$R^3$ and $R^4$, which are identical or different, are chosen from amongst a hydrogen atom and the group R as defined in the formula (I) or (II) of claim 1;

$R^5$ represents a hydroxyl, a halogen, an alcoxyl; or optionally $R^5$ forms with a cyclic group with $R^3$ or $R^4$.

5. The method for preparing a compound of claim 4, comprising:

(i) a step during which at least two equivalents of ethylene diamine or propylene diamine are made to react with at least one equivalent of a dicarbonyl compound having formula (IV) of claim 4, to form a bisaminal intermediate having formula (V) or (V') or a mixture of (V) and (V'):

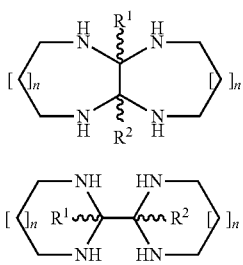

(V)

(V')

formulae (V) and (V') wherein $R^1$ and $R^2$ are as defined in the formula (IV) of claim 4;

(ii) a step during which the intermediate obtained is made to interact with a first cyclizing agent, and (iii) a step during which the novel intermediate obtained is made to react with the second cyclizing agent, where the steps (ii) and (iii) are performed simultaneously or successively, the cyclizing agent is identical or different and at least one of the two cyclizing agents meets the formula (VI) of claim 4.

6. The method according to claim 4, comprising the cyclizing agent having the formula (VI) is such that $R^5$ forms a cyclic group with $R^3$ or $R^4$ meeting one of the formulae (X) or (XI):

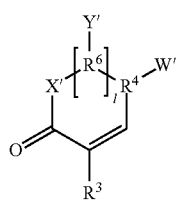

(X)

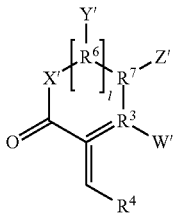

(XI)

formula (X) wherein: $R^3$ is a group R as defined in the formula (I) or (II) of claim 1, wherein:

X' is an oxygen atom,

Y' and W', identical or different, are chosen from amongst a hydrogen atom, a straight or branched, saturated or unsaturated $C_1$-$C_{30}$ alkyl group, l is equal to 0 or 1, wherein: when l is equal to 0, the group X' is linked to the group $R^4$ and $R^4$ forming with W' a group $CH_2$ or C=O, and when l is equal to 1, $R^4$ and $R^6$ together form, with the groups Y' and W', the groups $CH_2$—$CH_2$, CH=CH, $CH_2(C=O)$, $(C=O)CH_2$ or a phenyl group; and wherein $R^4$ of formula (XI) is a group R of formula (I) or (II) defined in claim 1, X' is an oxygen atom, W', Y' and Z', identical or different, are chosen from amongst a hydrogen atom, a straight or branched, saturated or unsaturated $C_1$-$C_{30}$ alkyl group, $R^3$, $R^6$ and $R^7$ designate $CH_2$ groups, l is equal to 0 or 1, wherein when l is equal to 1, $R^3$ and $R^7$ together form, with the groups Z' and W', the groups: $CH_2$—$CH_2$, CH=CH, or a phenyl group, and/or $R^6$ and $R^7$ together form, with the groups Y' and Z', the groups: $CH_2$—$CH_2$, CH=CH, or a phenyl group, and when l is equal to zero, the group X' is linked to the group $R^7$.

7. The method of claim 5, wherein the steps (i), (ii) and/or (iii) take place in a protic medium and/or are implemented at temperatures T1 and T2, below or equal to 100° C. with T1 being lower than T2, and/or are done without intermediate separation or purification steps.

8. The method of claim 4, wherein:

a C-functionalized and/or N-functionalized tetranitrogen cyclic compound is derived from cyclam, from a compound having formula (I), (II), one of its salts, solvates or their mixture comprising at least one of the following steps:

A) substituting one or more nitrogen atoms of the compound (I) and/or (II) by one or more groups R", identical or different, where R" designates any functional group or functional group precursor of claim 1, or any amine function protector group, B) reducing one or more ketone functions in alpha position of one of the four nitrogen atoms of the compound (I) and/or (II), said compound(s) (I) and/or (II) the optional step of being modified by one or more steps A) and/or C), C) deprotecting the bisaminal bridge of the compound(s) (I) and/or (II), said compound(s) (II) the optional step of being modified by one or more steps A) and/or B), the steps B) and C) being done simultaneously or separately.

9. The method of claim 8, comprising an additional step for reducing the compound having the formula (i) and/or (II) to a compound having the following formula (XII), one of its salts, solvates or mixture:

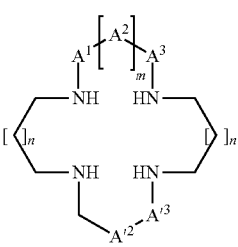

(XII)

wherein: $A^1$, $A^2$, $A^3$, $A'^2$, $A'^3$, identical or different, are chosen from the groups $CH_2$, CHR and C=O; on condition that $A'^2$ or $A'^3$ designates a CHR group; and m and n, identical or different, are equal to 0 or to 1.

10. The method of claim 8, wherein a compound having the following formula (XIII), one of its salts, solvates or mixture is prepared:

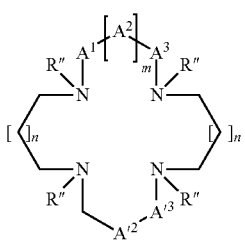

(XIII)

wherein: A¹, A², A³, A'², A'³, m and n are as defined in claim 1 where the groups R'', which are identical or different, designate a functional group R or a functional group precursor R as defined in claim 1, or a protector group of a nitrogen atom of the tetranitrogen cyclic compound, said method comprising the following steps:

i) reducing a compound having formula (I) or (II) as defined here above or their mixture, using at least one reducing agent, and ii) substituting, simultaneously or successively, on the four nitrogen atoms of the tetranitrogen cycle of the compound having a reduced formula (I) and/or (II) by groups R'', that are identical or different.

11. The method of claim 10, wherein a C-functionalized and N-mono-functionalized compound, one of its salts, solvates or their mixture, is prepared comprising the following steps:

(i) substituting a nitrogen atom of a compound having formula (I) and/or (II) by a protective group R'' as defined in the formula (XIII), then (ii) deprotecting the bisaminal bridge with hydrazine hydrate or sodium hydroxide, to obtain the following compound having formula (XIV), one of its salts, solvates or mixture:

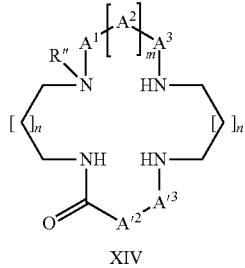

(XIV)

wherein: A¹, A², A³, A'², A'³, m and n are as defined in claim 1, the group R'' is as defined in the formula (XIII), and (iii) the optional step of reducing the compound having formula (XIV).

12. The method for preparing, according to claim 10, a C-functionalized and N-mono-functionalized compound, one of its salts, solvates or mixture, comprising the following steps:

(i) reducing a cyclic compound having formula (I) and/or (II), as defined in claim 1, or their mixture, using a selective reducing agent, then (ii) substituting on two non-adjacent nitrogen atoms of the tetranitrogen cycle having formula (I) or (II) or (I) and (II) reduced in case of mixture, or (III) by groups R'', and (iii) deprotecting the bisaminal bridge with hydrazine hydrate or sodium hydroxide to obtain a compound having the following formula (XV), one of its salts, solvates or mixture:

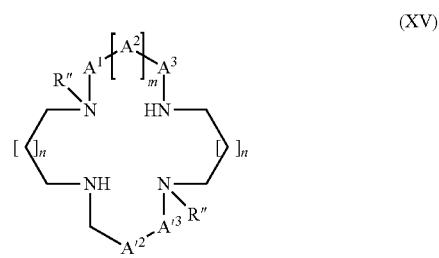

wherein: A¹, A², A³, A'², A'³, m and n are as defined in claim 1; the groups R'', which are identical or different, are as defined in the formula (XIII), (iv) and when R'' is an amine function protector group:

substituting the two non-substituted secondary amines of the compound (XV) by groups R''', identical or different, designating a functional group R'' or a functional group precursor R'', then deprotecting the protector groups R''.

13. The method for preparing, according to claim 10, a compound having the following formula (XVI), one of its salts, solvates or mixture:

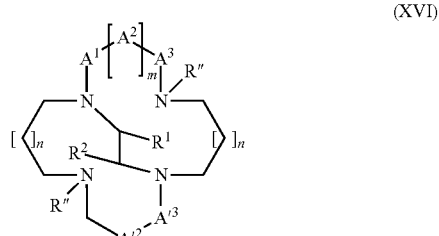

wherein: A¹, A², A³, A'², A'³, R¹ and R², m and n are as defined in the formula (I) or (II), the groups R'', which are identical or different, said method comprising the following steps (i) reducing the ketone function of a compound having formula (I) and/or (II) as defined in claim 1, using a selective reducing agent, then (ii) substituting the secondary amines of the compound having the reduced formula (I) and/or (II), and finally (iii) partially reducing the bisaminal bridge using a selective reducing agent.

14. A method for preparing a C-functionalized compound and one of either an N-mono or a di-functionalized compound, one of its salts, solvates or mixture, comprising the following steps:

(i) substituting a secondary amine of the compound having formula (I) and/or (II) by a group R'' as defined in the formula (XIII) in claim 10, then (ii) partially reducing the bisaminal bridge using a selective reducing agent, to obtain a compound having the formula (XVII), one of its salts, solvates or mixture:

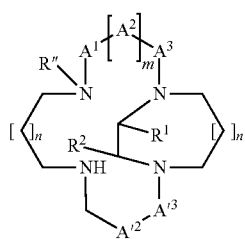

(XVII)

wherein: $A^1, A^2, A^3, A'^2, A'^3, R^1$ and $R^2$, m and n are as defined in the formula (I) or (II), the group R" is as defined in the formula (XIII) in claim 10, and (iii) the optional step of substituting the secondary amine of the compound (XVII) by a group R" as defined in the formula (XIII) defined in the claim 10, to obtain a compound having the formula (XVII'), one of its salts, solvates or mixture:

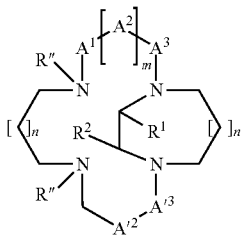

(XVII')

wherein: $A^1, A^2, A^3, A'^2, A'^3, R^1$ and $R^2$, m and n are as defined in the formula (I) or (II) defined in claim 1, the groups R", which are identical or different, are as defined in claim 10,

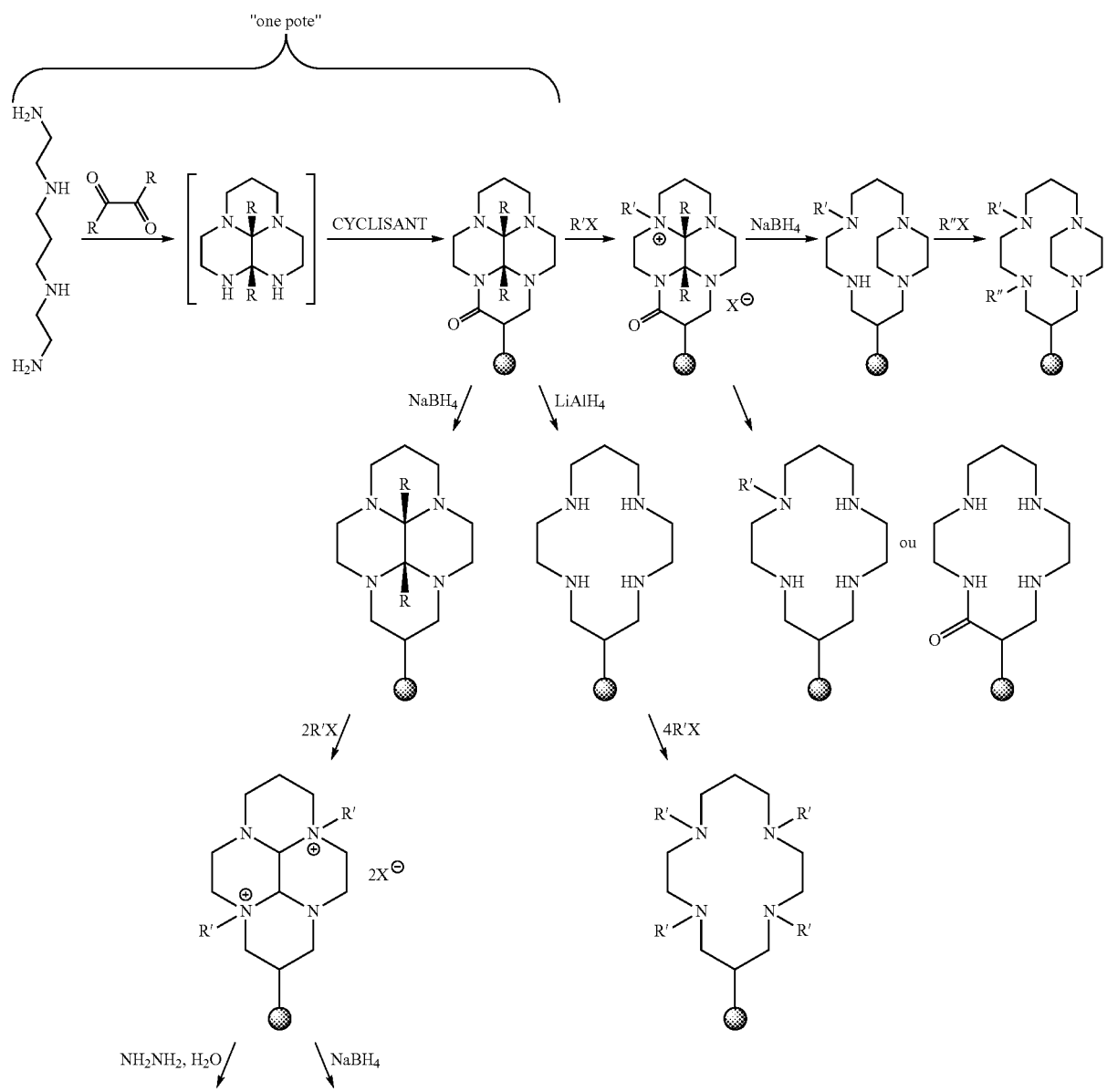

-continued
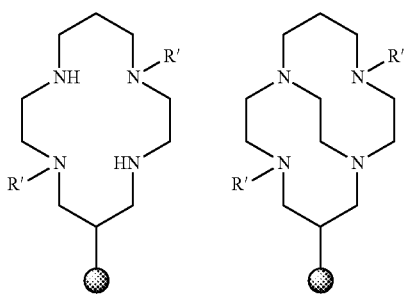
Fonction de couplage
R = Me ou H
R′ et R″ = fonctions ch latantes
"one pot operation"
Cyclizing
Fonction de couplage=Coupling function
R′ and R″=chelating functions.
* * * * *